Figure 1:
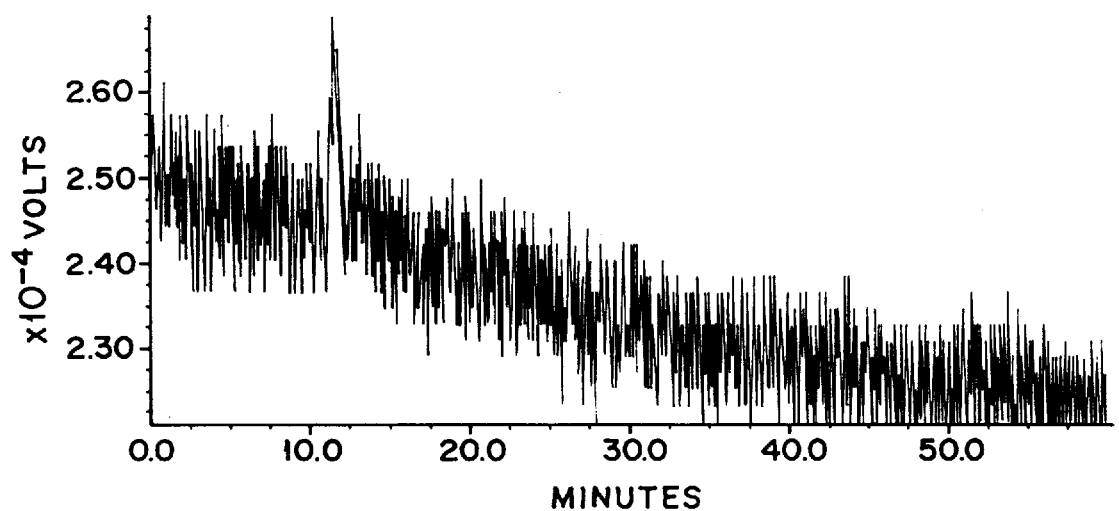

United States Patent [19]
Seki et al.

[11] Patent Number: 5,827,498
[45] Date of Patent: Oct. 27, 1998

[54] TUMOR AFFINITY PEPTIDE, AND RADIOACTIVE DIAGNOSTIC AGENT AND RADIOACTIVE THERAPEUTIC AGENT CONTAINING THE PEPTIDE

[75] Inventors: Ikuya Seki, Chiba; Yoshitoshi Itaya, Sodegaura; Yoshifumi Shirakami; Komei Washino, both of Ichihara, all of Japan

[73] Assignee: Nihon Medi-Physics Co., Ltd., Nishinomiya, Japan

[21] Appl. No.: 463,230

[22] Filed: Jun. 5, 1995

[30] Foreign Application Priority Data

Jun. 7, 1994 [JP] Japan .................................. 6-148655

[51] Int. Cl.⁶ ........................... A61K 51/00; A61M 36/14
[52] U.S. Cl. ..................... 424/1.69; 424/1.65; 530/300; 530/326; 530/327; 530/328
[58] Field of Search .................................. 424/1.11, 1.65, 424/1.69, 9.1; 530/300, 324–330; 534/10–16

[56] References Cited

FOREIGN PATENT DOCUMENTS

| 0 329 185 | 8/1989 | European Pat. Off. . |
|---|---|---|
| WO 90/05142 | 5/1990 | WIPO . |
| WO 90/10463 | 9/1990 | WIPO . |
| WO 92/13572 | 8/1992 | WIPO . |
| WO A 92 18534 | 10/1992 | WIPO . |
| wo 92/18534 | 10/1992 | WIPO . |

OTHER PUBLICATIONS

Synthetic Peptides Come of Age, The Journal of Nuclear Medicine, vol. 34, No. 11, pp. 15N, 18N, Nov. 1994.
Simona Ben–Haim et al., "The Safety and Pharmacokinetics in Adult Subjects of an Intravenously Administered $^{99m}$Tc–labeled 17 Amino Acid Peptide (CYT–379)", Nucl. Med. Biol., vol. 21, pp. 131–142, 1994.
Irene Virgolini, M.D., et al., "Vasoactive Intestinal Peptide–Receptor Imaging for the Localization of Intestinal Adenocarcinomas and Endocrine Tumors", The New England Journal of Medicine, Oct. 27, pp. 1116–1121, 1994.
Nucl. Med. Biol., vol. 20, No. 4, 1993, pp. 443–452.

*Primary Examiner*—John Kight
*Assistant Examiner*—Dameron Jones
*Attorney, Agent, or Firm*—Darby & Darby

[57] ABSTRACT

A peptide having affinity with tumor or a salt thereof, which comprises an amino acid sequence containing 20 or less amino acid residues, said amino acid sequence being described as $X_1$-YCAREPPT-$X_2$ wherein A, C, E, P, R, T and Y represent amino acid residues expressed by standard one-letter symbols, each of amino acid residues A, C, R and Y in the amino acid sequence YCAR may be in either L-form or D-form, $X_1$ represents a basic organic compound having 1–3 amino groups, and $X_2$ represents any given amino acid sequence, is provided together with a radioactive diagnostic agent and a radioactive therapeutic agent containing the above peptide or a salt thereof. The present tumor affinity peptide is high in radioactive metal labeling yield, useful for imaging and treating pathological tissues such as of breast cancer, ovarian cancer and colon cancer of mammals including human, and difficult to be readily metabolized in organisms and to accumulate in normal tissues especially at kidney and liver.

18 Claims, 9 Drawing Sheets

TUMOR

TUMOR

TUMOR AFFINITY PEPTIDE, AND RADIOACTIVE DIAGNOSTIC AGENT AND RADIOACTIVE THERAPEUTIC AGENT CONTAINING THE PEPTIDE

The present invention pertains to peptides having affinity with tumor, and salts thereof for use in imaging pathological tissues such as of tumors of mammals including human. It also relates to their radioactive metal-labeled peptides and salts thereof labeled with technetium-99m, rhenium-186, rhenium-188, copper-62 or indium-111, and radioactive metal-labeled diagnostic agents and radioactive metal-labeled therapeutic agents containing the radioactive metal-labeled peptides.

Tumor tissues are known to often exhibit proteins or complex carbohydrates specific to the tumor on the surface of the cells. Though these proteins or complex carbohydrates usually do not appear until the tissue turns malignant, there is also known the case where they are originally present in normal tissues and increase their amounts significantly as the tissue turns malignant. Therefore, many attempts have been made to construct monoclonal antibodies against those proteins or complex carbohydrates to specifically diagnose tumors. For example, in carcinoma of the colon and rectum in which CEA (Carcinoembryonic antigen) is significantly increased in expression, tumors were successfully detected in animal experiments or in clinical tests by a nuclear medicine technique using anti-CEA monoclonal antibody labeled with a radioactive metallic element, In-111. However, monoclonal antibodies, which are produced using cells of living organisms, require complicated processes and skills in handling, and therefore are not yet extensively utilized.

To overcome these circumstances, it would be more practical to analyze the antibody to determine a partial structure that contains a specific binding site, and to chemically synthesize the partial structure to prepare a reagent. From this point of view, a study is reported, which attempted to decipher peptide sequences of active centers of physiologically active substances such as naturally occurring proteins and anti-tumor monoclonal antibodies in order to reproduce binding capabilities equivalent to that of these proteins or anti-tumor monoclonal antibodies. (See *The Journal of Nuclear Medicine Newsline*, Lantz Miller, Vol. 34, No. 11, 15N–30N, 1993. 11, Synthetic Peptide Come of Age.)

Based on the above viewpoint, PCT/WO9218534-A discloses a peptide which has a binding capability equivalent to a monoclonal antibody (hereinafter referred to as "EPPT peptide"). Meanwhile, the amino acids are indicated using standard one-letter symbols or standard three-letter symbols in the present specification.

According to this reference, a monoclonal antibody specifically recognizing non-glycosylated mucin was prepared, and EPPT, which is a partial structure of the Complimentarity Determining Region (CDR) responsible for the specific binding of the antibody, was analyzed and determined.

The amino acid sequence derived from this CDR is described as YCAREPPTRTFAYWGQG, and the sequence labeled with iodine-125 is proven to be capable of binding to tumor cells, evidencing the possibility that it will be an alternative to the monoclonal antibody and will be a radioactive diagnostic agent of the next generation.

As radioactive isotopes which generally meet requirements for radioactive diagnostic agents, iodine-123, technetium-99m and so on can be exemplified. Especially, technetium-99m can be said to be the most suitable radioactive metal, since it emits 140 KeV of gamma rays which is suitable for taking scintigrams with an extensively used radioactivity imaging apparatus; it has a half life of 6 hours which is suitable in the field of nuclear medicine for imaging specific organs, detecting specific disorders and examining their movement; and it has an advantage that it is readily available at low price as its generators have become popular.

However, the previously-mentioned EPPT peptide still has some problems to be solved, for example, in that when it is labeled with technetium-99m or other radioactive metals, it does not have a labeling yield enough to be used as a medical product, and distributes radioactivity to normal tissues, especially kidney from the moment right after administration.

In view of the problems such as the low labeling yield of EPPT peptide labeled with technetium-99m and others and the accumulation of its catabolized products at normal tissues, especially kidney right after administration, the present invention aims at providing a tumor affinity peptide which is capable of being labeled with radioactive metals at a high labeling yield, which is not easily catabolized in the living body or accumulated at normal tissues, and which is useful for imaging and treating pathological tissues in the bodily trunk such as breast cancer, ovarian cancer and colon cancer of mammals including human. The present invention also aims at providing a radioactive metal-labeled peptide comprising said peptide and a radioactive metal, and a radioactive diagnostic agent and a radioactive therapeutic agent containing the peptide.

The present invention provides tumor affinity peptides having an amino acid sequence described as $X_1$-YCAREPPT-$X_2$ (hereinafter referred to as "formula 1") having up to 20 amino acid residues, and salts thereof. It also provides a radioactive metal-labeled peptide comprising a radioactive metal together with the above peptide or salts thereof, and further provides a radioactive diagnostic agent and a radioactive pharmaceutical agent containing the radioactive metal-labeled peptide. In the formula 1, $X_1$ is a basic organic compound having 1–3 amino groups, the amino acid sequence YCAR consists of amino acid residues Y, C, A and R each of which may be in L- and/or D-forms, and $X_2$ is any given amino acid sequence.

$X_1$ may be a basic organic compound derived by substituting amino groups for any given 1–3 hydrogen atoms of a saturated or unsaturated alkyl chain having 1–7 carbon atoms or of a saturated alkyl chain that has 1–7 carbon atoms and has been substituted by —OH and/or —COOH or —NH—C(NH)$NH_2$ group.

$X_1$ is bonded to the present peptide on N-terminal side thereof, and is preferably a basic amino acid having 1–3 amino groups, for example, K or R in L-form or D-form. $X_2$ may be any given amino acid sequence following the sequence YCAREPPT wherein amino acid residues Y, C, A and R may be in L-form and/or D-form, and is preferably RTNAYWG, RTFAYWG, RTNAYWGQG and RTFAYWGQG wherein each of the amino acid residues A, F, G, N, Q, R, T, W and Y may be in L-form and/or D-form. Further, the N-terminal or C-terminal of the present peptide may be chemically modified for the purpose of controlling retention time in blood.

For example, when $X_1$ is an amino acid, the chemical modification of the N-terminal can be made by acetylation, guanidylation, amidination, reduction alkylation, carbamylation, succinylation, maleilation, acetoacetylation, nitrotroponylation, dinitrophenylation, trinitrophenylation, benzyloxycarbonylation, t-butoxycarbonylation, 9-fluorenylmethoxycarbonylation, and preferably by acetylation.

Also, the C-terminal carboxyl group of $X_2$ may be chemically modified by amidation, esterification or alcoholization, more preferably, by amidation.

Moreover, the above mentioned peptide may form various cations, anions and salts when dissolved in aqueous solutions. Any form of the peptide is included in the present invention.

The tumor affinity peptide of the present invention can be obtained by synthesizing the peptide using a peptide synthesizer made by Applied Biosystems Inc., removing protective groups and beads at the same time from the peptide bound to the solid phase beads, and then purifying the peptide by high performance liquid chromatography (HPLC) using a reversed phase type column. The synthesis may also be effected by ordinary peptide solid phase methods such as Fmoc method.

The present peptide can be labeled for the purpose of diagnosis by dissolving it in physiological saline, an aqueous buffer or the like and reacting it with a radioactive metal. In case of technetium-99m, rhenium-186 or rhenium-188, labeled peptides can be prepared by an ordinary method of adding to said peptide a reducing agent having a suitable redox potential such as stannous chloride and mixing it with sodium pertechnetate solution or sodium perrhenate solution. In case of copper-62 or indium-111, labeled peptides can be prepared by mixing peptides with a neutral salt solution containing copper-62 ion or weak acidic aqueous solution containing indium-111 ion. Also, in case of yttrium-90, labeled peptides can be prepared by mixing said peptide with an aqueous solution of weak acid through weak base containing yttrium-90 ion. As required, impurities or unreacted pertechnetate ion, perrhenate ion, copper-62 ion, indium-111 ion and yttrium-90 ion may be removed by HPLC.

Furthermore, the present peptide may be supplied in a form of a kit so that it can be prepared as required. The kit may include stabilizers such as pharmaceutically acceptable ascorbic acid and p-amino-benzoic acid, pH adjusting agents such as aqueous buffers, excipients such as D-mannitol and promoting agents useful for improving radiochemical purity such as citric acid, tartaric acid and malonic acid.

The radioactive metal-labeled diagnostic agent containing the tumor affinity peptide of the present invention may be administered by generally-employed means of parenteral administration such as intravenous bolus injection. The amount of radioactivity to be administered can be so determined as to provide a sufficient count for imaging, taking into account various conditions such as patient's body weight and age and type of radioactive imaging apparatus. When the subject is human, a radioactivity from 185 MBq–1110 MBq is normally preferred.

Further, the radioactive metal-labeled therapeutic agent containing the tumor affinity peptide of the present invention may be administered by generally employed means of parenteral administration such as intravenous bolus injection. The amount of radioactivity to be administered can be so determined as to provide a radiation dose sufficient to enable the treatment, taking into account patient's body weight, age and sex, site of treatment and others. When the subject is human, a radioactivity is normally from 37 MBq to 18500 MBq, preferably from 370 MBq to 7400 MBq in case of rhenium-186 and rhenium-188. In case of yttrium-90, it is from 37 MBq to 3700 MBq, preferably 37 MBq to 1110 MBq. The present technique will be explained in more detail with respect to the examples below, in which amino acid residues in D-form will be described as D-amino acid residues, and

BRIEF DESCRIPTION OF THE DRAWING FIGURES

Figure 2:
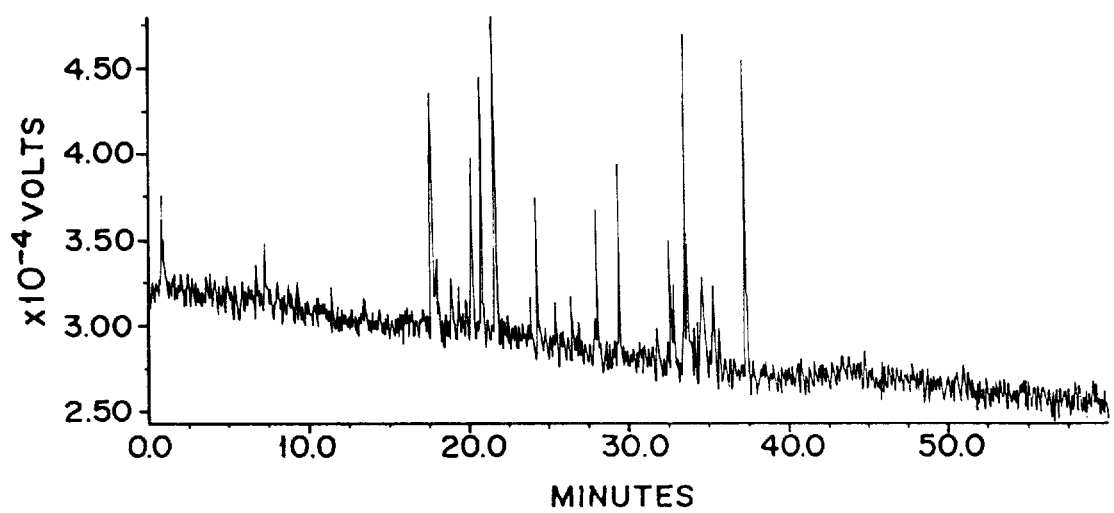
Figure 3:
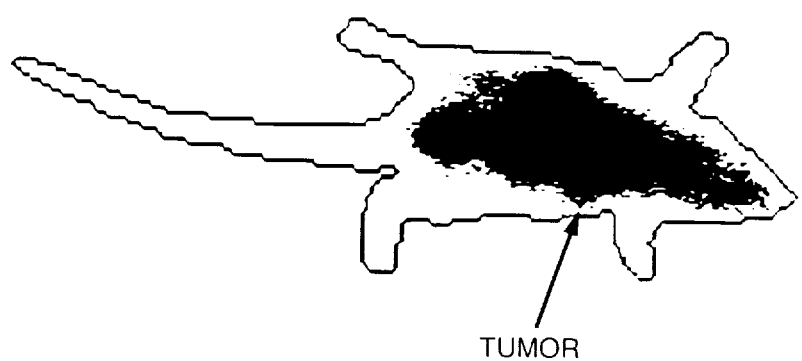
Figure 4:
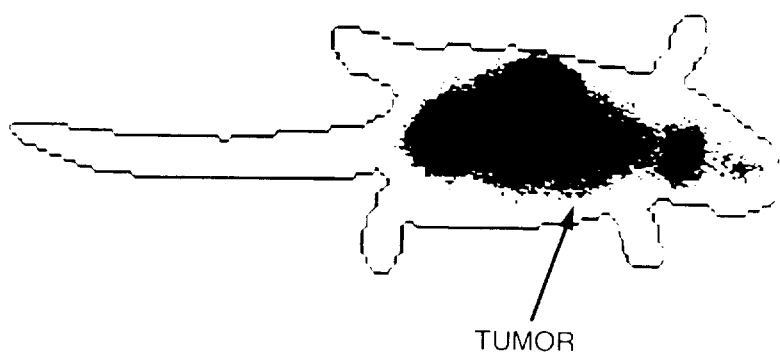
Figure 5:
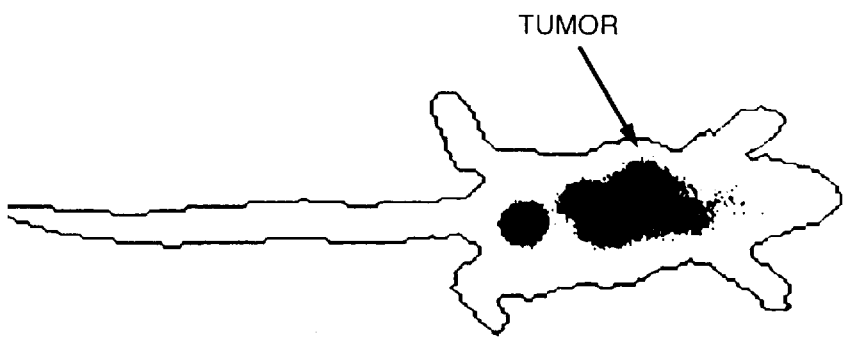
Figure 6:
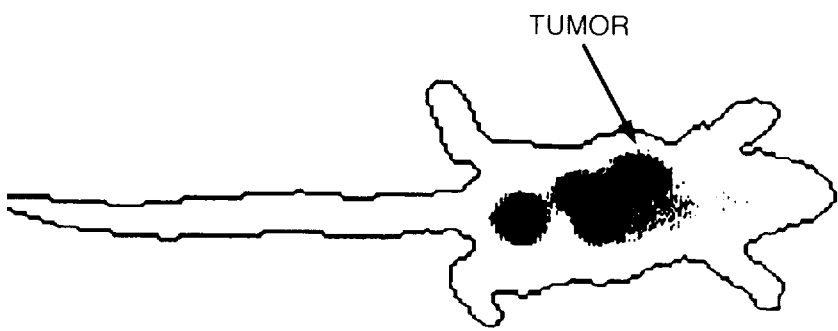
Figure 7:
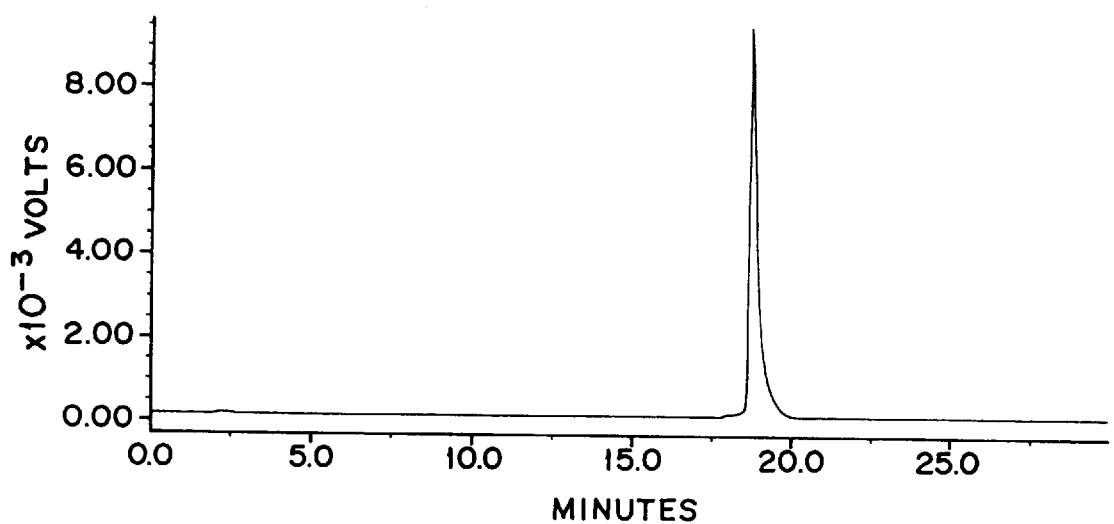
Figure 8:
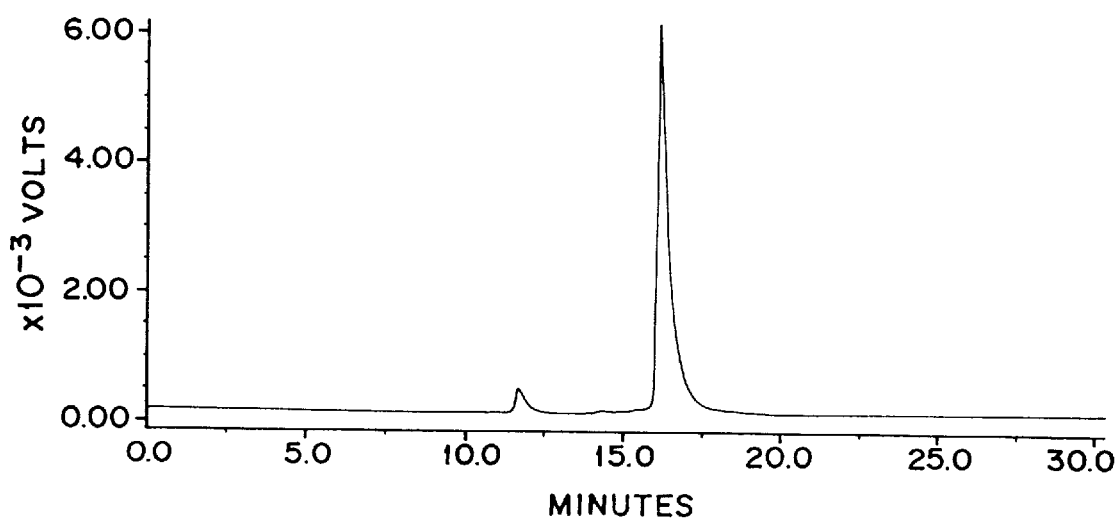
Figure 9:
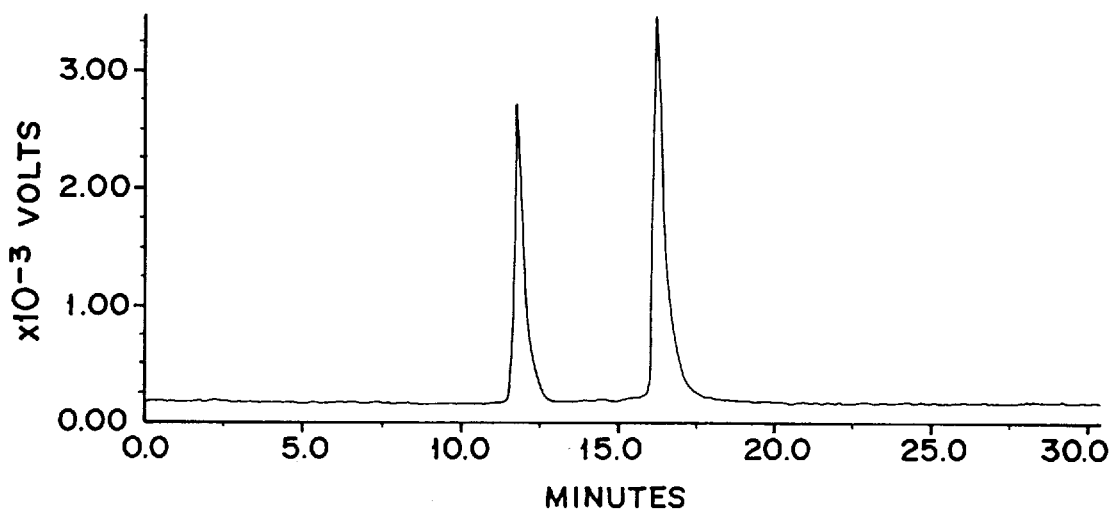
Figure 10:
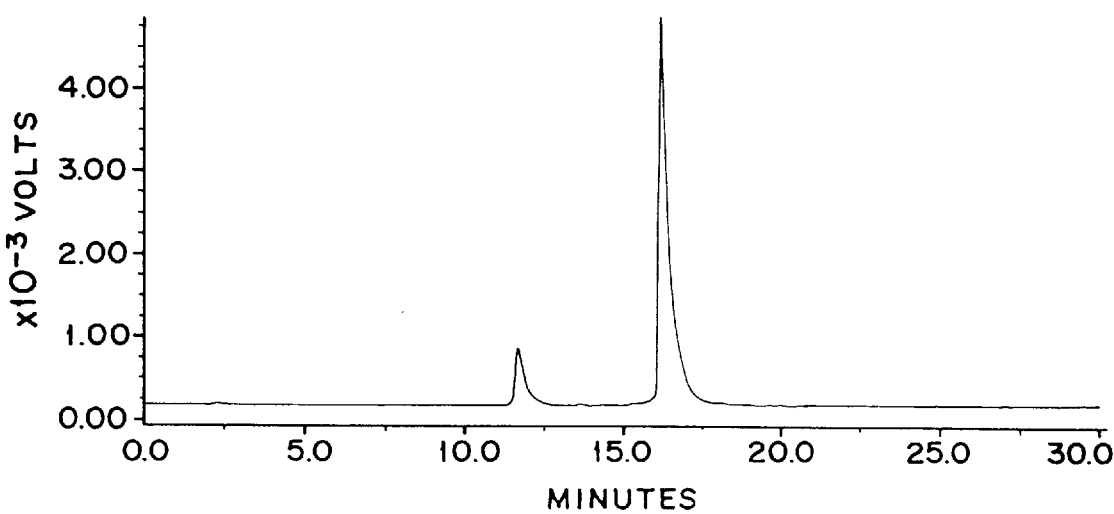
Figure 11:
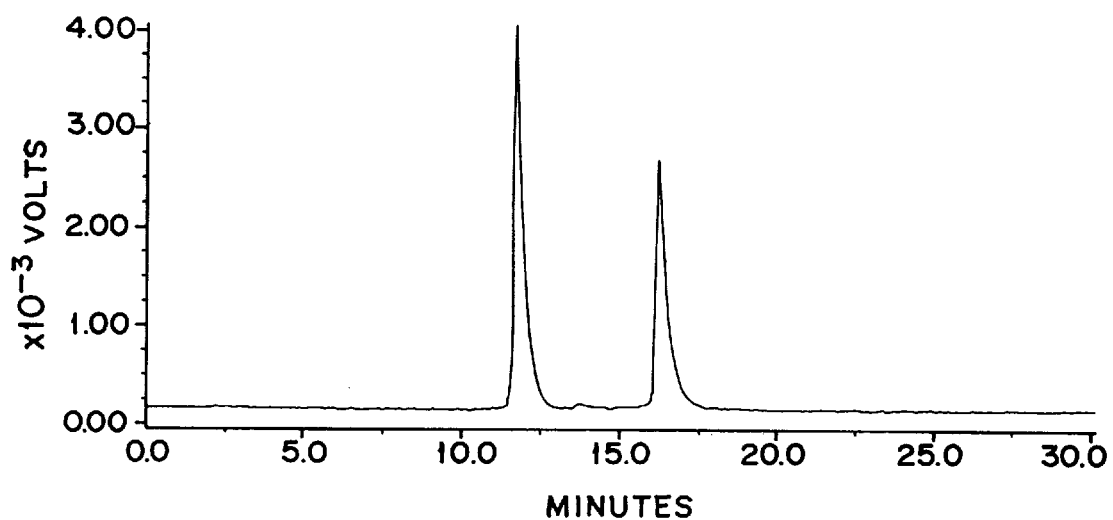
Figure 12:
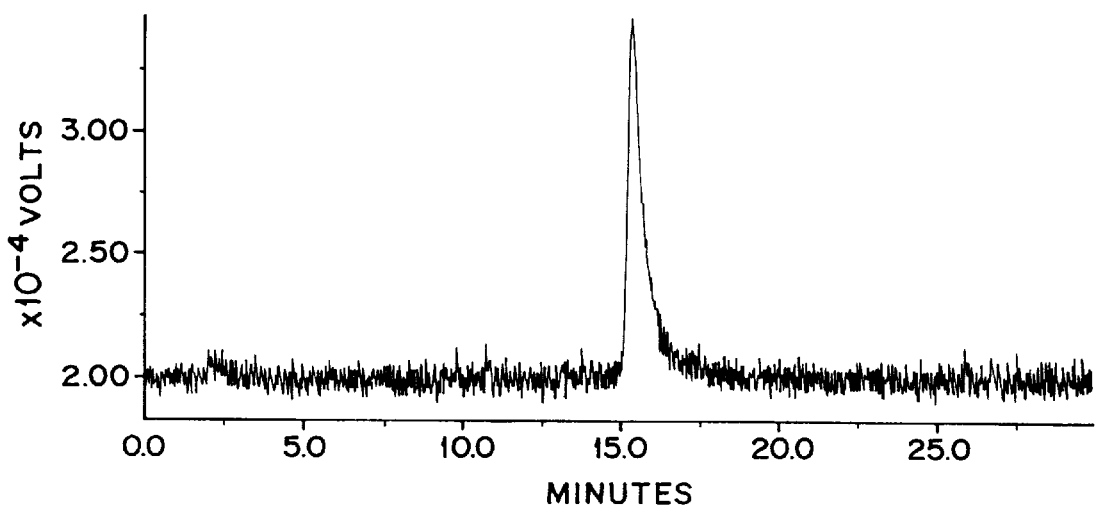
Figure 13:
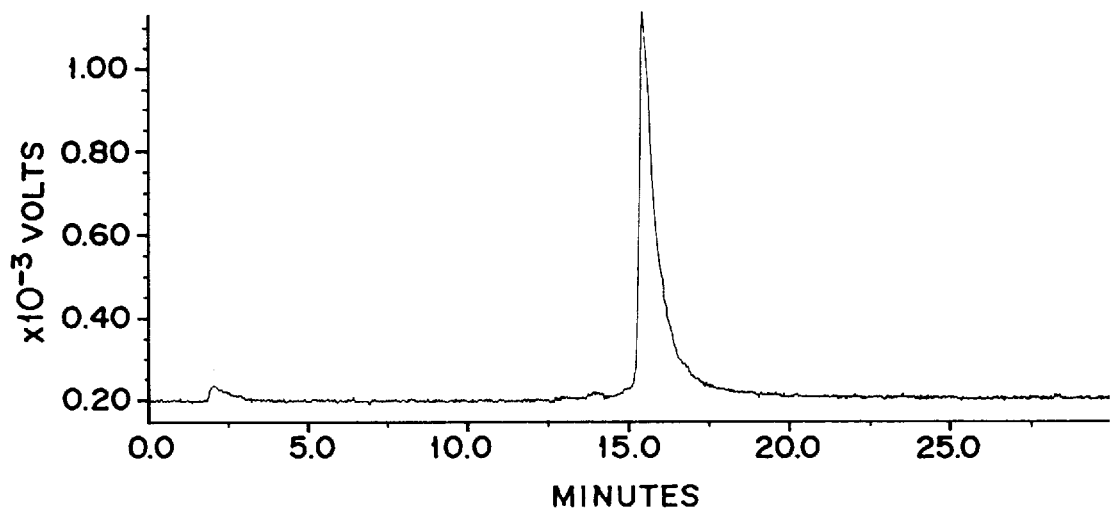
Figure 14:
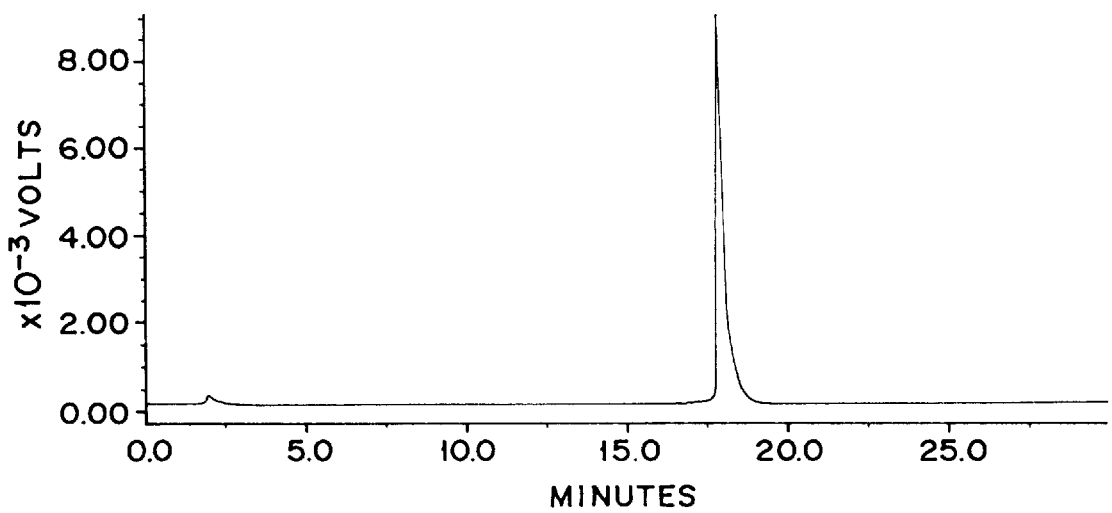
Figure 15:
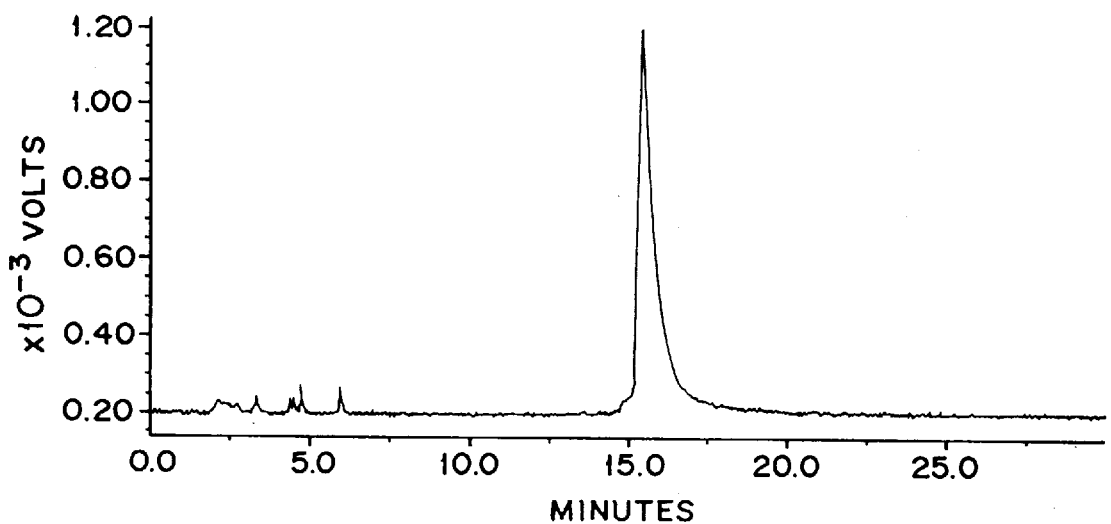

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is a chromatogram showing HPLC after administration of technetium-99m-peptide-1, FIG. 2 is a chromatogram showing HPLC after administration of technetium-99m-peptide-2, FIG. 3 is a scintigram showing a whole body of a nude mouse with laryngeal cancer at the 5-minute point after administration of technetium-99m-peptide-2, FIG. 4 is a scintigram showing a whole body of a nude mouse with laryngeal cancer at the 20-minute point after administration of technetium-99m-peptide-2, FIG. 5 is a scintigram showing a whole body of a nude mouse with laryngeal cancer at the 5-minute point after administration of technetium-99m-peptide-14, FIG. 6 is a scintigram showing a whole body of a nude mouse with laryngeal cancer at the 20-minute point after administration of technetium-99m-peptide-14, FIG. 7 is a chromatogram showing HPLC of technetium-99m-peptide-1, FIG. 8 is a chromatogram showing HPLC of a mixture of technetium-99m-peptide-1 and human plasma after incubation 5-minutes at 4° C., FIG. 9 is a chromatogram showing HPLC of a mixture of technetium-99m-peptide-1 and human plasma after incubation 30-minutes at 4° C., FIG. 10 is a chromatogram showing HPLC of a mixture of technetium-99m-peptide-1 and human plasma after incubation 5-minutes at 4° C., FIG. 11 is a chromatogram showing HPLC of a mixture of technetium-99m-peptide-1 and human plasma after incubation 30-minutes at 4° C., FIG. 12 is a chromatogram showing HPLC of a mixture of technetium-99m-peptide-8 and human plasma after incubation 5-minutes at 4° C., FIG. 13 is a chromatogram showing HPLC of a mixture of technetium-99m-peptide-8 and human plasma after incubation 30-minutes at 4° C., FIG. 14 is a chromatogram showing HPLC of a mixture of technetium-99m-peptide-8 and human plasma after incubation 5-minutes at 4° C., and FIG. 15 is a chromatogram showing HPLC of a mixture of technetium-99m-peptide-8 and human plasma after incubation 30-minutes at 4° C.

Figure 16:
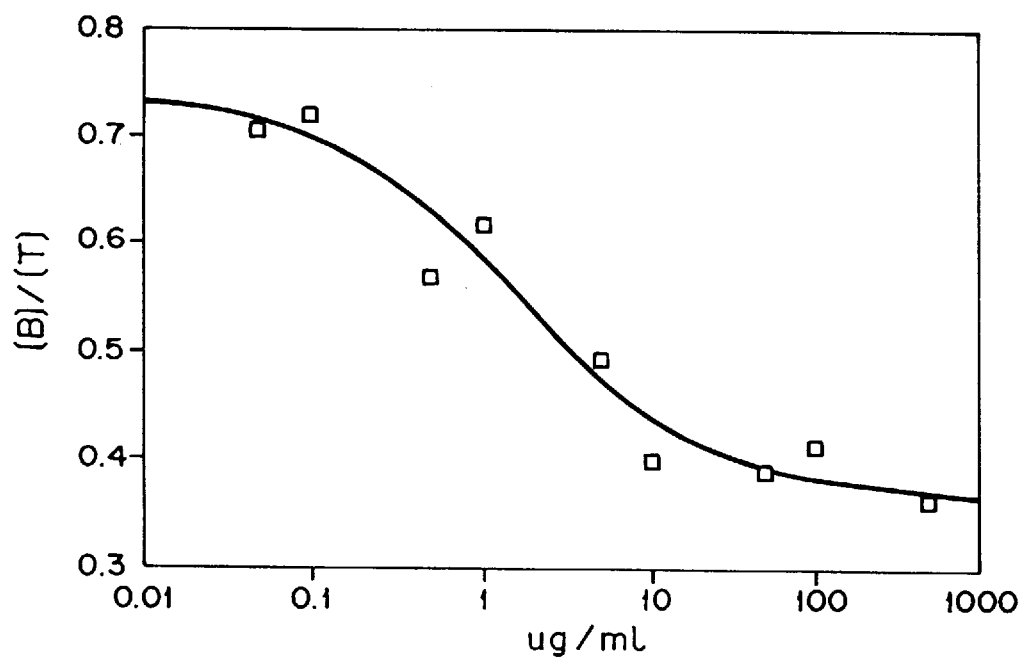
Figure 17:
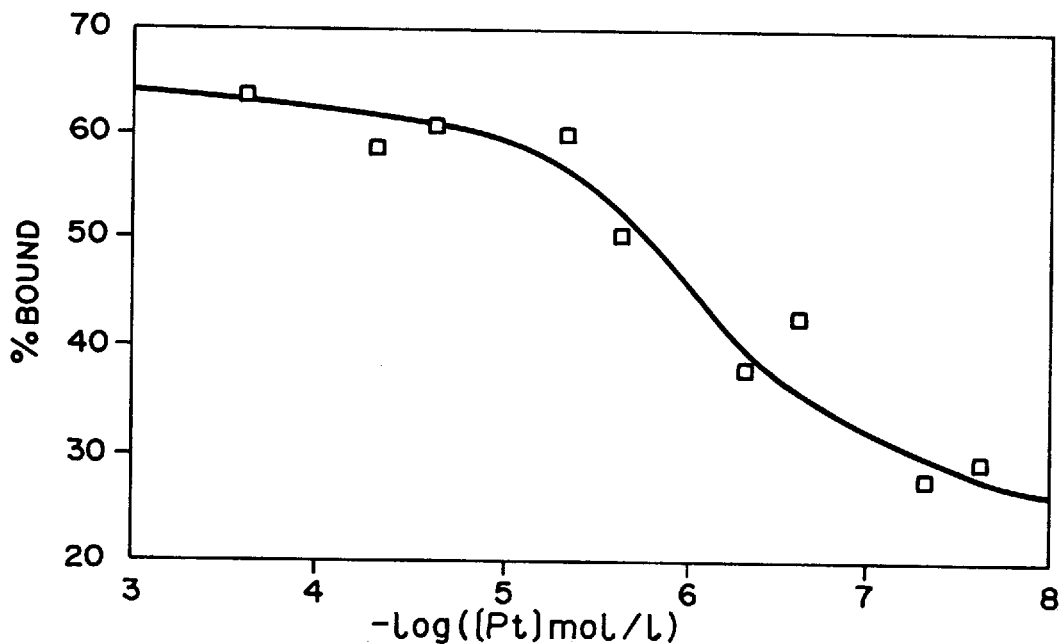
Figure 18:
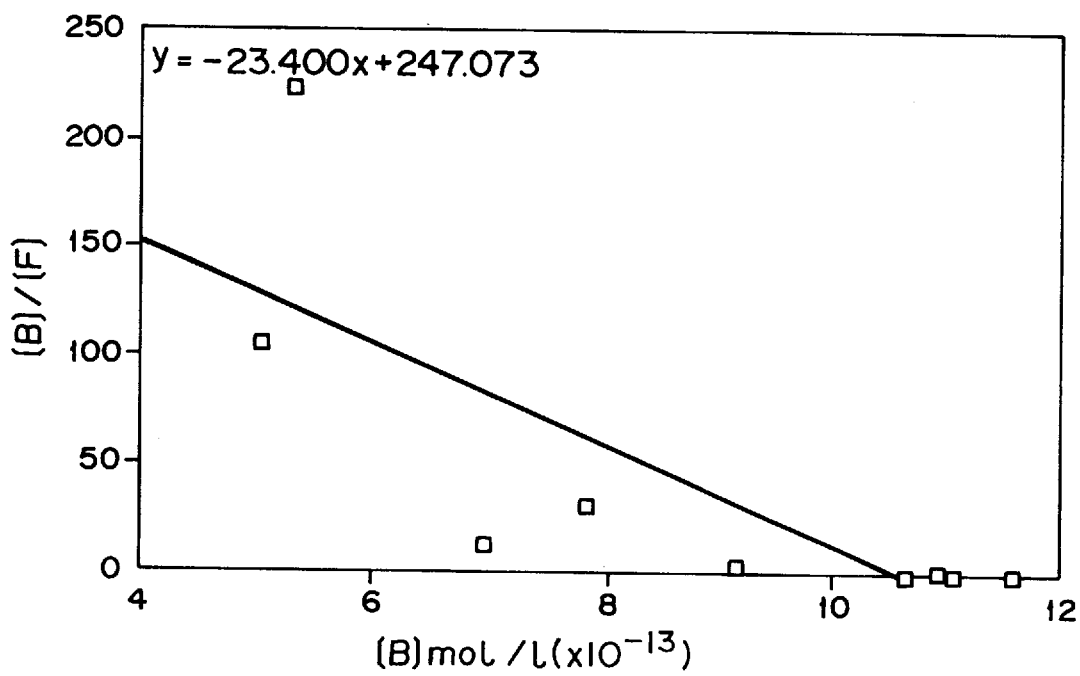

FIG. 16 is a diagram showing changes of radioactivity ratio with changes in concentration of peptide when peptide-14 was used, FIG. 17 is a diagram showing a saturation curve when peptide-14 is used, and FIG. 18 is a diagram showing a scatchard plot when peptide-14 is used.

EXAMPLE 1

Synthesis of KYCAREPPTRTFAYWGQG

The synthesis was conducted with a peptide synthesizer (Model 431A) produced by Applied Biosystems Inc. under 0.25 mM scale condition by Fmoc method using HMP resin (4-hydroxy-methyl-phenoxy methyl-copolystyrene-1% divinyl-benzene resin). Excision of the peptide was done by reaction for 1.0 hour in 82.6% aqueous trifluoroacetic acid (TFA) containing 6.5% phenol, 2.2% ethanedithiol (EDT) and 4.3% thioanisol. Purification was conducted using liquid chromatography (HPLC) under the following conditions:

Column: YMC-Pack R&DD-ODS-5-ST (20×150 mm),
Flow rate: 8 ml/min,
Eluent A: 0.1% TFA/purified water,
Eluent B: 0.1% TFA/acetonitrile,
Concentration gradient: 0 min. (15% B)→100 mins. (50% B)→120 mins. (75% B).

Alternatively, the synthesis was possible using preload resin instead of HMP resin.

Further, after determining the amino acid composition corresponding to the resulting main peak using PICO-TAG-TM-Workstation manufactured by Waters Inc. to confirm that it is the target peptide, the peak coinciding with the amino acid composition was lyophilized to yield 62.4 mg (29.3 μmol) of lyophilized product of KYCAREPPTRTFAY-WGQG (referred to as "peptide-1" hereinafter). The analytical value (number per molecule) for the amino acid composition of the resulting peptide is shown below together with the theoretical value (number per molecule) in parenthesis:

Peptide-1=Glx: 1.96 (2), Gly: 2.44 (2), Pro: 2.21 (2), Lys: 0.93 (1), Arg: 2.00 (2), Thr: 2.30 (2), Ala: 1.87 (2), Tyr: 2.14 (2), Cys: 0.35 (1), Phe: 0.93 (1), Trp: - (1).

In order to confirm the reliability of the peptide synthesizer, the amino acid sequence of the resulting peptide was determined using an automatic peptide analyzer manufactured by Applied Biosystems Inc. The result of the analysis showed that the sequence of the N-terminal until A of the 13th residue was identical with that of the target sequence. From the above, it was confirmed that the present peptide was the peptide having the amino acid sequence of KYCAREPPTRTFAYWGQG.

EXAMPLE 2

Syntheses of YCAREPPTRTNAYWG, YCAREPPTRTFAYWG and YCAREPPTRTFAYWGQG

After YCAREPPTRTNAYWG (hereinafter referred to as "peptide-2"), YCAREPPTRTFAYWG (hereinafter referred to as "peptide-3") and YCAREPPTRTFAYWGQG (hereinafter referred to as "peptide-4") were synthesized and the amino acid compositions thereof were determined according to the methods described in Example 1, the peaks coinciding with the amino acid compositions were lyophilized to obtain 42 mg (23.5 μmol) of lyophilized product of peptide-2, 40 mg (22 μmol) of lyophilized product of peptide-3 and 25 mg (12.5 μmol) of lyophilized product of peptide-4. The analytical values (number per molecule) of the amino acid compositions of the obtained peptides are shown below together with the theoretical values (number per molecule) in parentheses of the amino acid compositions of the target peptides.

Peptide-2=Asx: 1.11 (1), Glx: 1.04 (1), Gly: 1.09 (1), Arg: 2.0 (2), Thr: 2.07 (2), Ala: 1.93 (2), Pro: 1.88 (2), Tyr: 1.79 (2), Cys: 0.80 (1), Trp: - (1).

Peptide-3=Glx: 1.35 (1), Gly: 1.39 (1), Arg: 2.0 (2), Thr: 2.48 (2), Ala: 2.05 (2), Pro: 2.11 (2), Tyr: 1.79 (2), Cys: 0.68 (1), Phe: 1.22 (1), Trp: - (1).

Peptide-4=Glx: 1.98 (2), Gly: 1.95 (2), Arg: 2.30 (2), Thr: 1.84 (2), Ala: 1.89 (2), Pro: 2.30 (2), Tyr: 1.89 (2), Cys: 0.6 (1), Phe: 0.96 (1), Trp: - (1).

EXAMPLE 3

Syntheses of D-KYCAREPPTRTFAYWGD-QG, D-KD-YD-CAREPPTRTFAYWGQG, KYCAD-REPPTRTFAYWGQG, KYCAREPPTD-RTFAYWGQG, KYCAD-REPPTD-RTFAYWGOG, KYCAD-REPPTD-RTFAYD-WGQG, KYCAREPPTD-RTNAYWGQG, KYCAREPPTRD-TNAYWGQG, and KYCAREPPTRTNAD-YWGQG.

After synthesizing D-KYCAREPPTRTFAYWGD-QG (hereinafter referred to as "peptide-5"), D-KD-YD-CAREPPTRTFAYWGQG (hereinafter referred to as "peptide-6"), KYCAD-REPPTRTFAYWGQG (hereinafter referred to as "peptide-7"), KYCAREPPTD-RTFAYWGQG (hereinafter referred to as "peptide-8"), KYCAD-REPPTD-RTFAYWGQG (hereinafter referred to as "peptide-9"), KYCAD-REPPTD-RTFAYD-WGQG (hereinafter referred to as "peptide-10"), KYCAREPPTD-RTNAYWGQG (hereinafter referred to as "peptide-11"), KYCAREPPTRD-TNAYWGQG (hereinafter referred to as "peptide-12"), and KYCAREPPTRTNAD-YVGQG (hereinafter referred to as "peptide-13") and determining the amino acid compositions thereof according to the methods described in Example 1, the peaks coinciding with the amino acid compositions were lyophilized to obtain 47 mg (22.1 μmol) of lyophilized product of peptide-5, 11 mg (5.16 μmol) of lyophilized product of peptide-6, 29 mg (13.6 μmol) of lyophilized product of peptide-7, 32 mg (15.0 μmol) of lyophilized product of peptide-8, 74 mg (34.7 μmol) of lyophilized product of peptide-9, 67 mg (31.4 μmol) of lyophilized product of peptide-10, 38.2 mg (17.9 μmol) of lyophilized product of peptide-11, 37.7 mg (17.7 μmol) of lyophilized product of peptide-12, and 64.3 mg (30.9 μmol) of lyophilized product of peptide-13. The analytical values of the amino acid compositions (number per molecule) of the resulting peptides are shown below together with the theoretical values (number per molecule) in parentheses of the amino acid compositions of the target peptides.

Peptide-5=Glu: 1.96 (2), Gly: 2.18 (2), Arg: 1.93 (2), Thr: 1.95 (2), Ala: 2.05 (2), Pro: 2.11 (2), Tyr: 1.79 (2), Cys: - (1), Phe: 1.07 (1), Lys: 0.96 (1), Trp: - (1).

Peptide-6=Glu: 1.93 (2), Gly: 2.20 (2), Arg: 2.02 (2), Thr: 1.88 (2), Ala: 1.91 (2), Pro: 2.13 (2), Tyr: 1.89 (2), Cys: - (1), Phe: 1.09 (1), Lys: 0.96 (1), Trp: - (1).

Peptide-7=Glu: 1.98 (2), Gly: 2.18 (2), Arg: 1.84 (2), Thr: 2.01 (2), Ala: 1.90 (2), Pro: 2.15 (2), Tyr: 1.91 (2), Cys: - (1), Phe: 1.04 (1), Lys: 0.99 (1), Trp: - (1).

Peptide-8=Glu: 1.97 (2), Gly: 2.16 (2), Arg: 1.95 (2), Thr: 1.98 (2), Ala: 1.84 (2), Pro: 2.03 (2), Tyr: 2.06 (2), Cys: - (1), Phe: 1.01 (1), Lys: 0.99 (1), Trp: - (1).

Peptide-9=Glu: 1.85 (2), Gly: 2.05 (2), Arg: 1.93 (2), Thr: 2.09 (2), Ala: 2.01 (2), Pro: 2.01 (2), Tyr: 1.92 (2), Cys: - (1), Phe: 1.04 (1), Lys: 0.99 (1), Trp: - (1).

Peptide-10=Glu: 1.83 (2), Gly: 2.11 (2), Arg: 1.94 (2), Thr: 2.06 (2), Ala: 1.97 (2), Pro: 2.01 (2), Tyr: 1.93 (2), Cys: - (1), Phe: 1.04 (1), Lys: 1.00 (1), Trp: - (1).

Peptide-11=Asp: 0.96 (1), Glu: 1.97 (2), Gly: 2.18 (2), Arg: 1.98 (2), Thr: 2.11 (2), Ala: 1.89 (2), Pro: 2.00 (2), Tyr: 1.93 (2), Cys: - (1), Lys: 1.00 (1), Trp: - (1).

Peptide-12=Asp: 0.98 (1), Glu: 1.98 (2), Gly: 2.16 (2), Arg: 1.98 (2), Thr: 2.01 (2), Ala: 1.96 (2), Pro: 2.00 (2), Tyr: 1.94 (2), Cys: - (1), Lys: 0.99 (1), Trp: - (1).

Peptide-13=Asp: 0.96 (1), Glu: 1.97 (2), Gly: 2.18 (2), Arg: 2.00 (2), Thr: 1.99 (2), Ala: 2.05 (2), Pro: 2.04 (2), Tyr: 1.89 (2), Val: 0.95 (1), Cys: - (1), Lys: 0.97 (1).

EXAMPLE 4

Synthesis of C-terminal modified (amidated) peptide

In the method described in Example 1, PAL resin (Peptide Amide Linker) made Milligen Bioresearch Inc. was employed instead of HMP resin to synthesize peptide-1 with the C-terminal thereof being amidated. Excision of the peptide was done by reaction for 1.5 hour in 82.6% aqueous trifluoroacetic acid (TFA) containing 6.5% phenol, 2.2% ethanedithiol (EDT) and 4.3% thioanisol. Purification was conducted using liquid chromatography (HPLC method) under the following conditions:

Column: YMC-Pack ODS-SH-343-5 (20×250 mm),
Flow rate: 8 ml/min,
Eluent A: 0.1% TFA/purified water,
Eluent B: 0.1% TFA/acetonitrile,
Concentration gradient: 0 min. (10% B)→10 mins. (10% B)→50 mins. (75% B)→60 mins. (90% B).

The amino acid composition was determined according to the method described in Example 1 and then the peak coinciding with the amino acid composition was lyophilized to obtain 10 mg (4.6 μmol) of lyophilized product of the C-terminal amidated peptide-1.

EXAMPLE 5

Synthesis of C-terminal modified (amidated) and N-terminal modified (acetylated) peptide After synthesizing peptide-1 with the C-terminal thereof being amidated according to the method described in Example 4, the N-terminal thereof was acetylated by acetic anhydride using N-hydroxybenzotriasol (HOBt) as an activator, which was followed by excision. The excision of the peptide was done by the method described in Example 4. Analysis of amino acid composition was conducted by the method described in Example 1 and the peak coinciding with the amino acid composition was lyophilized to obtain 10 mg (4.5 μmol) of lyophilized product of C-terminal amidated and N-terminal acetylated peptide-1.

EXAMPLE 6

Preparation of synthesized peptide labeled with technetium-99m

To 40.3 μmol/300 μl of glucoheptanate was added 130 nmol/50 μl of stannous chloride and 1049 MBq of sodium pertechnetate, and the entire volume was adjusted to 1.3 ml. After stirring, the mixture was left to stand still for 30 minutes at room temperature and then the labeling purity of glucoheptanate was confirmed to be 95% or more by cellulose acetate membrane electrophoresis. 242 MBq/300 μl of the mixture was added to 0.46 μmol/300 μl of peptide-1 obtained in Example 1 and the reaction was completed in a hot water bath at 100° C. in 20 minutes to yield the target technetium-99m-peptide-1. After cooling at room temperature, the peptide was confirmed to have a labeling purity of 98.3% according to HPLC method.

EXAMPLE 7

Comparison of technetium-99m labeling yield among peptide-1, peptide-2, peptide-3 and peptide-4 in vitro After technetium-99m-peptide-1 obtained in Example 6 and technetium-99m-peptides-2 to 4 obtained by the same method as in Example 6 were left to stand still for 1, 3 and 6 hours, the time course changes of technetium-99m labeling yield of the peptides were studied using liquid chromatography (HPLC method) under the following conditions:

Column: Millipore puresil 5 μm C18 (4.6×150 mm),
Flow rate: 1 ml/min,
Eluent A: 0.1% TFA/purified water,
Eluent B: 0.1% TFA/acetonitrile,
Concentration gradient: 0 min. (10% B)→5 mins. (10% B)→35 mins. (50% B)→45 mins. (75% B). The results are shown in Table 1.

TABLE 1

Time course of technetium-99m labeling yield in peptide-1, peptide-2, peptide-3 and peptide-4

|  | 1 hr. | 3 hr. | 6 hr. |
| --- | --- | --- | --- |
| Peptide-1 | 98.3% | 97.2% | 96.6% |
| Peptide-2 | 85.5% | 71.8% | 78.5% |
| Peptide-3 | 96.3% | 88.9% | 84.4% |
| Peptide-4 | 81.5% | 81.2% | 79.9% |

The result reveals instability of the labels in peptide-2, peptide-3 and peptide-4 and their great degradation with the passage of time, indicating that their labeling yield 3 hours after preparation are below 95% which is the critical labeling yield for medical use. In contrast, the labeling yield of peptide-1 of the present invention was high, i.e., 98% or more at the 1 hour point after the labeling and 96% or more even at the 6 hour point after the labeling, confirming that the peptide-1 is stable and maintains high labeling yield with the passage of time.

EXAMPLE 8

Comparison of in vivo kinetics among technetium-99m labeled peptide-1, peptide-2, peptide-3, peptide-4, peptide-5, peptide-6, peptide-7, peptide-8, peptide-9, peptide-10, peptide-11, peptide-12, peptide-13 and KYCAREPPTRTNAYWGQG To SD rats (Sprague-Dawley Rats) weighing 140 to 200 grams and previously Ravonal anesthetized, technetium-99m-peptide-1 obtained in Example 6, technetium-99m-peptide-2, 3 and 4 obtained in Example 7, technetium-99m-peptide-5, 6, 7, 8, 9, 10, 11, 12, 13 and KYCAREPPTRTNAYWGQG (hereinafter referred to as "peptide-14") prepared according to the method of Example 6 were each administered to the tail vein in an amount of 35 MBq to 45 MBq. The animals were sacrificed 5, 30, 60 and 180 minutes later to determine distribution ratio of radioactivity in various organs using a single channel counter. The results are shown in Tables 2–29.

In case of technetium-99m-peptide-1 shown in Tables 2–3, 20% and 80% of the total radioactivity were respectively excreted into urine at the 5 and 60 minute points after administration. No significant concentration of radioactivity in the other organs was observed and no accumulation of radioactivity was detected.

In case of technetium-99m-peptide-2 shown in Tables 4–5, approximately 3.0% and 33% of the total radioactivity were respectively excreted into urine at the 5 and 60 minute points after administration. Accumulation of radioactivity was observed in few organs but approximately 29% and 49% of the total radioactivity were respectively concentrated into kidneys at the 5 and 60 minute points after administration.

In case of technetium-99m-peptide-3 shown in Tables 6–7, approximately 4.0% and 42% of the total radioactivity were respectively excreted into urine at the 5 and 60 minute points after administration. Further, approximately 18% of the total radioactivity administered was accumulated in kidneys almost constantly until the 180 minute point. Uptake of radioactivity into livers and small intestines was also detected.

In case of technetium-99m-peptide-4 shown in Tables 8–9, approximately 2.0% and 28% of the total radioactivity were respectively excreted into urine at the 5 and 60 minute point after administration. Further, approximately 16% and 32% of the total radioactivity were respectively accumulated at kidneys at the 5 and 60 minute points after administration. Uptake of radioactivity into livers and small intestines was also detected. Technetium-99m-peptide-4 was considered to be placed between peptide-2 and peptide-3 in terms of in vivo kenetics.

In case of technetium-99m-peptide-14 shown in Tables 28–29, approximately 13% and 68% of the total radioactivity were respectively excreted into urine at the 5 and 60 minute points after administration. No substantial accumulation in internal organs was found as evidenced by the tendency of successive decrease in radioactivity at kidneys, i.e., approximately 13% and 8% of the total radioactivity at the 5 and 60 minute points respectively.

From the above, it is apparent that technetium-99m-peptide-1 and technetium-99m-peptide-14, which are peptides of the present invention, are low in accumulation at internal organs such as kidney and liver, are excreted into urine quickly after administration, and show in vivo kenetics desirable for use as a radioactive diagnostic agent, whereas technetium-99m-peptides-2 to 4 are high in accumulation at internal organs especially kidney and thus have undesirable properties for diagnosing the bodily trunk.

Furthermore, as is shown in Tables 14, 15, 18, 19, 20 and 21 among Tables 1 to 21, peptides-7, 9 and 10, in which Arg of the 5th amino acid residue is in D-form, showed reduced percentages of radioactivity in liver and small intestines compared with peptides having corresponding L-Arg, and was promoted in transportation into excretion channel of the renal system. This result suggests that the peptides-7, 9 and 10 have in vivo kinetic useful as a desirable radioactive diagnostic agent for abdominal imaging with low background.

TABLE 2

Biodistribution of technetium-99m-peptide-1 in normal rats (n = 3)

|  | 5 mins. | 30 mins. |
|---|---|---|
| liver | 3.63 ± 1.75 | 2.88 ± 0.56 |
|  | (0.58 ± 0.28) | (0.43 ± 0.05) |
| small intestine | 2.75 ± 0.78 | 3.14 ± 0.65 |
|  | (0.40 ± 0.09) | (0.48 ± 0.12) |
| large intestine | 1.63 ± 0.38 | 0.56 ± 0.08 |
|  | (0.23 ± 0.03) | (0.10 ± 0.03) |
| stomach | 0.65 ± 0.22 | 0.45 ± 0.14 |
|  | (0.27 ± 0.06) | (0.16 ± 0.05) |
| pancreas | 0.33 ± 0.20 | 0.14 ± 0.06 |
|  | (0.82 ± 0.51) | (0.34 ± 0.15) |
| lung | 1.09 ± 0.52 | 0.45 ± 0.09 |
|  | (1.10 ± 0.45) | (0.48 ± 0.07) |
| heart | 0.29 ± 0.08 | 0.12 ± 0.01 |
|  | (0.49 ± 0.11) | (0.20 ± 0.02) |
| kidney | 9.65 ± 1.99 | 6.80 ± 0.84 |
|  | (8.06 ± 2.66) | (5.36 ± 0.31) |
| whole blood | 17.38 ± 1.58 | 6.85 ± 1.68 |
|  | (1.56 ± 0.07) | (0.62 ± 0.14) |
| the rest of the body | 50.31 ± 2.82 | 25.57 ± 2.55 |
|  | (0.39 ± 0.03) | (0.20 ± 0.03) |
| urine | 19.46 ± 8.85 | 55.55 ± 4.91 |

*% ID/organ (% ID/g)

TABLE 3

Biodistribution of technetium-99m-peptide-1 in normal rats (n = 3)

|  | 60 mins. | 180 mins. |
|---|---|---|
| liver | 1.77 ± 0.68 | 0.99 ± 0.50 |
|  | (0.27 ± 0.12) | (0.15 ± 0.07) |
| small intestine | 3.69 ± 0.16 | 2.09 ± 0.48 |
|  | (0.53 ± 0.02) | (0.29 ± 0.09) |
| large intestine | 0.24 ± 0.01 | 3.55 ± 1.22 |
|  | (0.04 ± 0.00) | (0.51 ± 0.16) |
| stomach | 0.36 ± 0.23 | 0.66 ± 0.04 |
|  | (0.13 ± 0.08) | (0.02 ± 0.01) |
| pancreas | 0.09 ± 0.05 | 0.06 ± 0.04 |
|  | (0.20 ± 0.12) | (0.16 ± 0.10) |
| lung | 0.19 ± 0.08 | 0.07 ± 0.04 |
|  | (0.22 ± 0.10) | (0.08 ± 0.04) |
| heart | 0.04 ± 0.01 | 0.01 ± 0.00 |
|  | (0.06 ± 0.01) | (0.01 ± 0.00) |
| kidney | 5.22 ± 0.93 | 4.75 ± 1.08 |
|  | (3.97 ± 0.64) | (3.69 ± 0.54) |
| whole blood | 2.06 ± 0.33 | 0.37 ± 0.14 |
|  | (0.18 ± 0.03) | (0.03 ± 0.01) |
| the rest of the body | 8.39 ± 1.12 | 2.20 ± 1.51 |
|  | (0.18 ± 0.03) | (0.20 ± 0.01) |
| urine | 78.81 ± 0.99 | 86.01 ± 3.07 |

*% ID/organ (% ID/g)

TABLE 4

Biodistribution of technetium-99m-peptide-2 in normal rats (n = 3)

|  | 5 mins. | 30 mins. |
|---|---|---|
| liver | 4.30 ± 0.17 | 2.39 ± 0.37 |
|  | (0.69 ± 0.04) | (0.37 ± 0.06) |
| small intestine | 2.97 ± 0.32 | 2.16 ± 0.17 |
|  | (0.43 ± 0.06) | (0.33 ± 0.05) |
| large intestine | 1.48 ± 0.14 | 0.61 ± 0.12 |
|  | (0.25 ± 0.06) | (0.11 ± 0.01) |
| stomach | 0.60 ± 0.48 | 0.44 ± 0.25 |
|  | (0.25 ± 0.17) | (0.15 ± 0.08) |
| pancreas | 0.19 ± 0.02 | 0.08 ± 0.01 |
|  | (0.46 ± 0.06) | (0.22 ± 0.07) |
| lung | 0.95 ± 0.32 | 0.38 ± 0.09 |
|  | (1.12 ± 0.32) | (0.46 ± 0.07) |
| heart | 0.34 ± 0.02 | 0.15 ± 0.03 |
|  | (0.50 ± 0.01) | (0.25 ± 0.04) |
| kidney | 28.57 ± 2.36 | 45.10 ± 3.65 |
|  | (22.28 ± 2.34) | (37.15 ± 2.83) |
| whole blood | 19.10 ± 1.86 | 6.71 ± 1.00 |
|  | (1.75 ± 0.22) | (0.64 ± 0.10) |
| the rest of the body | 46.23 ± 1.97 | 24.52 ± 4.92 |
|  | (0.37 ± 0.03) | (0.20 ± 0.03) |
| urine | 2.95 ± 0.49 | 20.17 ± 3.87 |

*% ID/organ (% ID/g)

TABLE 5

Biodistribution of technetium-99m-peptide-2 in normal rats (n = 3)

|  | 60 mins. | 180 mins. |
|---|---|---|
| liver | 1.76 ± 0.19 | 0.93 ± 0.06 |
|  | (0.27 ± 0.03) | (0.15 ± 0.01) |
| small intestine | 2.46 ± 0.06 | 2.27 ± 0.27 |
|  | (0.38 ± 0.02) | (0.36 ± 0.02) |
| large intestine | 0.27 ± 0.05 | 10471 ± 0.14 |
|  | (0.04 ± 0.00) | (0.23 ± 0.02) |
| stomach | 0.18 ± 0.06 | 0.06 ± 0.01 |
|  | (0.05 ± 0.02) | (0.03 ± 0.01) |
| pancreas | 0.04 ± 0.01 | 0.02 ± 0.00 |
|  | (0.11 ± 0.01) | (0.06 ± 0.00) |
| lung | 0.17 ± 0.02 | 0.08 ± 0.01 |
|  | (0.21 ± 0.01) | (0.09 ± 0.01) |

TABLE 5-continued

Biodistribution of technetium-99m-peptide-2 in normal rats (n = 3)

|  | 60 mins. | 180 mins. |
|---|---|---|
| heart | 0.07 ± 0.01 | 0.03 ± 0.00 |
|  | (0.12 ± 0.01) | (0.04 ± 0.00) |
| kidney | 48.87 ± 7.80 | 42.46 ± 0.33 |
|  | (42.92 ± 7.78) | (32.32 ± 0.78) |
| whole blood | 2.98 ± 0.63 | 1.23 ± 0.26 |
|  | (0.28 ± 0.04) | (0.10 ± 0.01) |
| the rest of the body | 11.24 ± 1.55 | 4.73 ± 0.68 |
|  | (0.09 ± 0.01) | (0.04 ± 0.01) |
| urine | 33.22 ± 6.05 | 47.27 ± 0.92 |

*% ID/organ (% ID/g)

TABLE 6

Biodistribution of technetium-99m-peptide-3 in normal rats (n = 3)

|  | 5 mins. | 30 mins. |
|---|---|---|
| liver | 18.33 ± 2.86 | 10.21 ± 0.95 |
|  | (3.09 ± 0.36) | (1.76 ± 0.23) |
| small intestine | 3.17 ± 0.39 | 6.85 ± 1.01 |
|  | (0.50 ± 0.06) | (1.10 ± 0.11) |
| large intestine | 1.41 ± 0.16 | 0.63 ± 0.02 |
|  | (0.27 ± 0.06) | (0.09 ± 0.01) |
| stomach | 0.68 ± 0.18 | 0.63 ± 0.37 |
|  | (0.25 ± 0.07) | (0.20 ± 0.10) |
| pancreas | 0.21 ± 0.04 | 0.15 ± 0.02 |
|  | (0.59 ± 0.08) | (0.25 ± 0.12) |
| lung | 1.03 ± 0.15 | 0.49 ± 0.06 |
|  | (1.24 ± 0.21) | (0.54 ± 0.04) |
| heart | 0.35 ± 0.05 | 0.16 ± 0.03 |
|  | (0.65 ± 0.08) | (0.28 ± 0.06) |
| kidney | 17.83 ± 1.74 | 19.64 ± 1.14 |
|  | (14.54 ± 0.85) | (16.58 ± 1.62) |
| whole blood | 15.16 ± 2.00 | 9.04 ± 0.69 |
|  | (1.60 ± 0.20) | (0.92 ± 0.08) |
| the rest of the body | 43.53 ± 1.53 | 23.06 ± 1.05 |
|  | (0.31 ± 0.01) | (0.20 ± 0.01) |
| urine | 3.81 ± 1.22 | 32.94 ± 1.97 |

*% ID/organ (% ID/g)

TABLE 7

Biodistribution of technetium-99m-peptide-3 in normal rats (n = 3)

|  | 60 mins. | 180 mins. |
|---|---|---|
| liver | 10.99 ± 4.55 | 3.80 ± 0.95 |
|  | (1.73 ± 0.74) | (0.62 ± 0.15) |
| small intestine | 10.39 ± 4.32 | 13.87 ± 0.67 |
|  | (1.51 ± 0.58) | (2.00 ± 0.22) |
| large intestine | 0.42 ± 0.21 | 0.64 ± 0.34 |
|  | (0.06 ± 0.02) | (0.08 ± 0.04) |
| stomach | 1.11 ± 0.79 | 0.24 ± 0.11 |
|  | (0.33 ± 0.27) | (0.07 ± 0.03) |
| pancreas | 0.10 ± 0.01 | 0.08 ± 0.02 |
|  | (0.24 ± 0.04) | (0.19 ± 0.04) |
| lung | 0.28 ± 0.05 | 0.22 ± 0.07 |
|  | (0.34 ± 0.06) | (0.24 ± 0.06) |
| heart | 0.09 ± 0.01 | 0.05 ± 0.01 |
|  | (0.15 ± 0.02) | (0.08 ± 0.03) |
| kidney | 18.29 ± 4.21 | 16.13 ± 1.33 |
|  | (14.77 ± 3.37) | (12.83 ± 2.52) |
| whole blood | 5.77 ± 1.40 | 3.26 ± 0.31 |
|  | (0.56 ± 0.13) | (0.30 ± 0.05) |
| the rest of the body | 13.29 ± 1.75 | 8.02 ± 2.30 |
|  | (0.11 ± 0.01) | (0.07 ± 0.02) |
| urine | 41.78 ± 3.38 | 55.45 ± 3.89 |

*% ID/organ (% ID/g)

TABLE 8

Biodistribution of technetium-99m-peptide-4 in normal rats (n = 3)

|  | 5 mins. | 30 mins. |
|---|---|---|
| liver | 16.03 ± 3.89 | 6.84 ± 0.89 |
|  | (2.72 ± 0.70) | (1.14 ± 0.24) |
| small intestine | 3.03 ± 0.75 | 4.11 ± 0.36 |
|  | (0.45 ± 0.11) | (0.60 ± 0.05) |
| large intestine | 1.37 ± 0.39 | 1.13 ± 0.20 |
|  | (0.22 ± 0.07) | (0.18 ± 0.02) |
| stomach | 1.00 ± 0.46 | 1.42 ± 0.34 |
|  | (0.30 ± 0.13) | (0.40 ± 0.08) |
| pancreas | 0.30 ± 0.09 | 0.31 ± 0.06 |
|  | (0.77 ± 0.19) | (0.74 ± 0.11) |
| lung | 1.36 ± 0.32 | 0.94 ± 0.08 |
|  | (1.61 ± 0.28) | (1.12 ± 0.11) |
| heart | 0.36 ± 0.18 | 0.24 ± 0.04 |
|  | (0.66 ± 0.27) | (0.44 ± 0.07) |
| kidney | 15.54 ± 5.35 | 25.27 ± 3.87 |
|  | (12.86 ± 3.90) | (21.52 ± 4.08) |
| whole blood | 23.26 ± 3.51 | 11.31 ± 7.17 |
|  | (2.30 ± 0.36) | (1.07 ± 0.66) |
| the rest of the body | 45.47 ± 2.16 | 36.18 ± 4.85 |
|  | (0.38 ± 0.02) | (0.29 ± 0.04) |
| urine | 1.89 ± 1.50 | 17.58 ± 2.96 |

*% ID/organ (% ID/g)

TABLE 9

Biodistribution of technetium-99m-peptide-4 in normal rats (n = 3)

|  | 60 mins. | 180 mins. |
|---|---|---|
| liver | 3.85 ± 0.59 | 2.77 ± 0.16 |
|  | (0.60 ± 0.04) | (0.46 ± 0.03) |
| small intestine | 5.30 ± 0.77 | 9.06 ± 1.32 |
|  | (0.82 ± 0.07) | (1.24 ± 0.09) |
| large intestine | 0.65 ± 0.10 | 0.68 ± 0.29 |
|  | (0.09 ± 0.01) | (0.10 ± 0.06) |
| stomach | 1.05 ± 0.31 | 1.06 ± 0.46 |
|  | (0.32 ± 0.12) | (0.27 ± 0.08) |
| pancreas | 0.18 ± 0.03 | 0.16 ± 0.03 |
|  | (0.38 ± 0.04) | (0.36 ± 0.06) |
| lung | 0.60 ± 0.12 | 0.30 ± 0.03 |
|  | (0.70 ± 0.15) | (0.34 ± 0.02) |
| heart | 0.16 ± 0.03 | 0.10 ± 0.01 |
|  | (0.28 ± 0.04) | (0.15 ± 0.02) |
| kidney | 31.77 ± 0.97 | 27.06 ± 1.43 |
|  | (24.55 ± 1.98) | (19.57 ± 0.29) |
| whole blood | 7.73 ± 1.30 | 4.49 ± 0.57 |
|  | (0.72 ± 0.14) | (0.40 ± 0.06) |
| the rest of the body | 23.96 ± 1.55 | 14.21 ± 0.41 |
|  | (0.19 ± 0.01) | (0.11 ± 0.04) |
| urine | 28.07 ± 1.42 | 42.20 ± 1.96 |

*% ID/organ (% ID/g)

TABLE 10

Biodistribution of technetium-99m-peptide-5 in normal rats (n = 3)

|  | 5 mins. | 30 mins. |
|---|---|---|
| liver | 3.36 ± 0.15 | 1.68 ± 0.08 |
|  | (0.49 ± 0.01) | (0.23 ± 0.02) |
| small intestine | 2.36 ± 0.14 | 3.04 ± 0.82 |
|  | (0.31 ± 0.01) | (0.36 ± 0.09) |
| large intestine | 1.41 ± 0.10 | 0.44 ± 0.06 |
|  | (0.18 ± 0.02) | (0.05 ± 0.01) |
| stomach | 0.62 ± 0.12 | 0.28 ± 0.10 |
|  | (0.19 ± 0.06) | (0.07 ± 0.03) |
| pancreas | 0.30 ± 0.02 | 0.15 ± 0.03 |
|  | (0.64 ± 0.02) | (0.30 ± 0.06) |
| lung | 0.73 ± 0.04 | 0.28 ± 0.05 |
|  | (0.80 ± 0.03) | (0.30 ± 0.06) |

TABLE 10-continued

Biodistribution of technetium-99m-peptide-5 in normal rats (n = 3)

|  | 5 mins. | 30 mins. |
| --- | --- | --- |
| heart | 0.31 ± 0.07 | 0.11 ± 0.05 |
|  | (0.48 ± 0.07) | (0.16 ± 0.06) |
| kidney | 11.67 ± 2.57 | 7.71 ± 0.52 |
|  | (8.66 ± 1.82) | (5.41 ± 0.33) |
| whole blood | 14.60 ± 1.51 | 5.01 ± 0.49 |
|  | (1.23 ± 0.14) | (0.41 ± 0.03) |
| the rest of the body | 48.92 ± 4.39 | 19.70 ± 3.20 |
|  | (0.35 ± 0.03) | (0.14 ± 0.03) |
| urine | 20.75 ± 2.46 | 63.68 ± 4.32 |

*% ID/organ (% ID/g)

TABLE 11

Biodistribution of technetium-99m-peptide-5 in normal rats (n = 3)

|  | 60 mins. | 180 mins. |
| --- | --- | --- |
| liver | 1.67 ± 0.08 | 1.39 ± 0.06 |
|  | (0.25 ± 0.02) | (0.23 ± 0.00) |
| small intestine | 4.08 ± 0.61 | 5.93 ± 2.06 |
|  | (0.60 ± 0.10) | (0.98 ± 0.39) |
| large intestine | 0.31 ± 0.09 | 0.30 ± 0.15 |
|  | (0.04 ± 0.01) | (0.04 ± 0.02) |
| stomach | 0.17 ± 0.13 | 0.02 ± 0.01 |
|  | (0.08 ± 0.06) | (0.01 ± 0.01) |
| pancreas | 0.14 ± 0.01 | 0.11 ± 0.02 |
|  | (0.34 ± 0.03) | (0.27 ± 0.04) |
| lung | 0.13 ± 0.03 | 0.04 ± 0.01 |
|  | (0.14 ± 0.02) | (0.05 ± 0.00) |
| heart | 0.03 ± 0.00 | 0.01 ± 0.00 |
|  | (0.05 ± 0.00) | (0.01 ± 0.00) |
| kidney | 5.72 ± 1.13 | 5.03 ± 0.20 |
|  | (4.14 ± 0.67) | (4.04 ± 0.07) |
| whole blood | 1.73 ± 0.77 | 0.13 ± 0.04 |
|  | (0.15 ± 0.07) | (0.01 ± 0.00) |
| the rest of the body | 8.36 ± 1.76 | 1.96 ± 1.75 |
|  | (0.06 ± 0.01) | (0.02 ± 0.01) |
| urine | 78.34 ± 3.08 | 85.13 ± 4.07 |

*% ID/organ (% ID/g)

TABLE 12

Biodistribution of technetium-99m-peptide-6 in normal rats (n = 3)

|  | 5 mins. | 30 mins. |
| --- | --- | --- |
| liver | 2.81 ± 0.40 | 1.65 ± 0.39 |
|  | (0.43 ± 0.03) | (0.26 ± 0.08) |
| small intestine | 3.01 ± 0.11 | 2.78 ± 0.38 |
|  | (0.44 ± 0.03) | (0.40 ± 0.07) |
| large intestine | 1.60 ± 0.17 | 0.96 ± 0.27 |
|  | (0.22 ± 0.02) | (0.13 ± 0.05) |
| stomach | 1.59 ± 0.31 | 2.93 ± 0.59 |
|  | (0.41 ± 0.19) | (1.10 ± 0.14) |
| pancreas | 0.17 ± 0.04 | 0.11 ± 0.05 |
|  | (0.37 ± 0.07) | (0.25 ± 0.13) |
| lung | 0.87 ± 0.09 | 0.34 ± 0.06 |
|  | (1.06 ± 0.07) | (0.40 ± 0.03) |
| heart | 0.46 ± 0.09 | 0.13 ± 0.01 |
|  | (0.71 ± 0.12) | (0.21 ± 0.01) |
| kidney | 13.01 ± 1.41 | 8.22 ± 0.40 |
|  | (10.95 ± 0.62) | (6.86 ± 0.60) |
| whole blood | 16.95 ± 3.26 | 6.27 ± 0.65 |
|  | (1.58 ± 0.26) | (0.61 ± 0.06) |
| the rest of the body | 55.68 ± 1.63 | 25.21 ± 3.72 |
|  | (0.45 ± 0.03) | (0.21 ± 0.03) |
| urine | 10.81 ± 2.32 | 53.83 ± 4.53 |

*% ID/organ (% ID/g)

TABLE 13

Biodistribution of technetium-99m-peptide-6 in normal rats (n = 3)

|  | 60 mins. | 180 mins. |
| --- | --- | --- |
| liver | 1.25 ± 0.44 | 0.43 ± 0.02 |
|  | (0.21 ± 0.08) | (0.08 ± 0.00) |
| small intestine | 3.89 ± 0.67 | 3.22 ± 1.27 |
|  | (0.56 ± 0.07) | (0.54 ± 0.19) |
| large intestine | 1.08 ± 0.41 | 1.11 ± 0.84 |
|  | (0.16 ± 0.06) | (0.17 ± 0.11) |
| stomach | 0.35 ± 1.20 | 4.42 ± 0.41 |
|  | (1.16 ± 0.38) | (1.63 ± 0.32) |
| pancreas | 0.05 ± 0.01 | 0.02 ± 0.01 |
|  | (0.12 ± 0.02) | (0.05 ± 0.06) |
| lung | 0.20 ± 0.06 | 0.04 ± 0.01 |
|  | (0.22 ± 0.05) | (0.05 ± 0.01) |
| heart | 0.08 ± 0.02 | 0.01 ± 0.00 |
|  | (0.13 ± 0.04) | (0.02 ± 0.00) |
| kidney | 7.89 ± 0.53 | 6.23 ± 0.57 |
|  | (6.07 ± 0.48) | (5.04 ± 0.52) |
| whole blood | 3.45 ± 1.01 | 0.66 ± 0.43 |
|  | (0.37 ± 0.35) | (0.07 ± 0.04) |
| the rest of the body | 19.83 ± 0.45 | 3.42 ± 0.24 |
|  | (0.17 ± 0.01) | (0.03 ± 0.00) |
| urine | 61.50 ± 5.80 | 80.68 ± 1.38 |

*% ID/organ (% ID/g)

TABLE 14

Biodistribution of technetium-99m-peptide-7 in normal rats (n = 3)

|  | 5 mins. | 30 mins. |
| --- | --- | --- |
| liver | 2.15 ± 0.32 | 1.00 ± 0.39 |
|  | (0.32 ± 0.04) | (0.16 ± 0.06) |
| small intestine | 3.25 ± 0.37 | 1.46 ± 0.65 |
|  | (0.44 ± 0.04) | (0.23 ± 0.11) |
| large intestine | 2.37 ± 0.32 | 2.43 ± 1.43 |
|  | (0.32 ± 0.06) | (0.32 ± 0.19) |
| stomach | 0.73 ± 0.07 | 0.30 ± 0.12 |
|  | (0.21 ± 0.04) | (0.09 ± 0.04) |
| pancreas | 0.15 ± 0.03 | 0.07 ± 0.01 |
|  | (0.38 ± 0.05) | (0.16 ± 0.06) |
| lung | 0.90 ± 0.24 | 0.36 ± 0.14 |
|  | (1.00 ± 0.15) | (0.40 ± 0.18) |
| heart | 0.42 ± 0.13 | 0.12 ± 0.06 |
|  | (0.66 ± 0.15) | (0.22 ± 0.11) |
| kidney | 10.79 ± 0.52 | 7.60 ± 3.17 |
|  | (9.16 ± 1.08) | (6.84 ± 3.15) |
| whole blood | 16.57 ± 0.38 | 6.09 ± 3.08 |
|  | (1.57 ± 0.06) | (0.59 ± 0.30) |
| the rest of the body | 57.52 ± 2.45 | 18.22 ± 5.01 |
|  | (0.47 ± 0.02) | (0.15 ± 0.04) |
| urine | 11.49 ± 0.63 | 65.07 ± 4.31 |

*% ID/organ (% ID/g)

TABLE 15

Biodistribution of technetium-99m-peptide-7 in normal rats (n = 3)

|  | 60 mins. | 180 mins. |
| --- | --- | --- |
| liver | 1.08 ± 0.33 | 0.23 ± 0.03 |
|  | (0.19 ± 0.07) | (0.05 ± 0.01) |
| small intestine | 0.59 ± 0.08 | 0.75 ± 0.12 |
|  | (0.09 ± 0.02) | (0.12 ± 0.01) |
| large intestine | 0.23 ± 0.06 | 0.15 ± 0.01 |
|  | (0.03 ± 0.01) | (0.02 ± 0.00) |
| stomach | 0.11 ± 0.04 | 0.07 ± 0.02 |
|  | (0.03 ± 0.02) | (0.02 ± 0.01) |
| pancreas | 0.03 ± 0.02 | 0.01 ± 0.00 |
|  | (0.09 ± 0.05) | (0.03 ± 0.01) |
| lung | 0.09 ± 0.04 | 0.02 ± 0.00 |
|  | (0.10 ± 0.04) | (0.02 ± 0.00) |

TABLE 15-continued

Biodistribution of technetium-99m-peptide-7 in normal rats (n = 3)

|  | 60 mins. | 180 mins. |
| --- | --- | --- |
| heart | 0.03 ± 0.01 | 0.01 ± 0.00 |
|  | (0.05 ± 0.02) | (0.01 ± 0.00) |
| kidney | 4.78 ± 1.11 | 2.97 ± 0.18 |
|  | (4.04 ± 0.64) | (2.73 ± 0.32) |
| whole blood | 1.05 ± 0.35 | 0.06 ± 0.05 |
|  | (0.10 ± 0.04) | (0.01 ± 0.01) |
| the rest of the body | 8.49 ± 1.76 | 1.69 ± 0.51 |
|  | (0.07 ± 0.02) | (0.02 ± 0.01) |
| urine | 83.96 ± 1.58 | 94.08 ± 0.58 |

*% ID/organ (% ID/g)

TABLE 16

Biodistribution of technetium-99m-peptide-8 in normal rats (n = 3)
* % ID/organ (% ID/g)

|  | 5 mins. | 30 mins. |
| --- | --- | --- |
| liver | 2.28 ± 0.37 | 1.51 ± 0.37 |
|  | (0.29 ± 0.05) | (0.20 ± 0.07) |
| small intestine | 2.82 ± 0.37 | 2.16 ± 0.48 |
|  | (0.31 ± 0.04) | (0.26 ± 0.08) |
| large intestine | 1.72 ± 0.15 | 0.62 ± 0.07 |
|  | (0.21 ± 0.03) | (0.07 ± 0.02) |
| stomach | 0.79 ± 0.05 | 0.34 ± 0.15 |
|  | (0.21 ± 0.04) | (0.14 ± 0.09) |
| pancreas | 0.19 ± 0.02 | 0.07 ± 0.01 |
|  | (0.34 ± 0.05) | (0.13 ± 0.01) |
| lung | 1.01 ± 0.10 | 0.35 ± 0.04 |
|  | (0.96 ± 0.07) | (0.33 ± 0.06) |
| heart | 0.38 ± 0.08 | 0.13 ± 0.04 |
|  | (0.53 ± 0.07) | (0.19 ± 0.05) |
| kidney | 10.28 ± 0.68 | 5.62 ± 0.74 |
|  | (7.43 ± 1.10) | (3.95 ± 0.36) |
| whole blood | 21.01 ± 1.34 | 6.80 ± 0.85 |
|  | (1.43 ± 0.09) | (0.48 ± 0.06) |
| the rest of the body | 55.03 ± 2.00 | 25.84 ± 3.60 |
|  | (0.31 ± 0.02) | (0.15 ± 0.02) |
| urine | 14.34 ± 3.41 | 59.86 ± 4.96 |

TABLE 17

Biodistribution of technetium-99m-peptide-8 in normal rats (n = 3)
* % ID/organ (% ID/g)

|  | 60 mins. | 180 mins. |
| --- | --- | --- |
| liver | 0.93 ± 0.17 | 0.31 ± 0.03 |
|  | (0.25 ± 0.02) | (0.05 ± 0.00) |
| small intestine | 4.01 ± 0.81 | 2.99 ± 1.20 |
|  | (0.52 ± 0.13) | (0.39 ± 0.10) |
| large intestine | 0.39 ± 0.15 | 0.37 ± 0.25 |
|  | (0.05 ± 0.02) | (0.04 ± 0.03) |
| stomach | 0.15 ± 0.01 | 0.03 ± 0.01 |
|  | (0.04 ± 0.01) | (0.01 ± 0.00) |
| pancreas | 0.04 ± 0.01 | 0.02 ± 0.00 |
|  | (0.08 ± 0.01) | (0.04 ± 0.01) |
| lung | 0.18 ± 0.06 | 0.03 ± 0.00 |
|  | (0.17 ± 0.05) | (0.03 ± 0.00) |
| heart | 0.06 ± 0.02 | 0.01 ± 0.00 |
|  | (0.08 ± 0.02) | (0.02 ± 0.01) |
| kidney | 5.70 ± 1.50 | 4.12 ± 0.62 |
|  | (4.19 ± 1.17) | (3.23 ± 0.13) |
| whole blood | 2.60 ± 1.12 | 0.45 ± 0.44 |
|  | (0.19 ± 0.07) | (0.03 ± 0.03) |

TABLE 17-continued

Biodistribution of technetium-99m-peptide-8 in normal rats (n = 3)
* % ID/organ (% ID/g)

|  | 60 mins. | 180 mins. |
| --- | --- | --- |
| the rest of the body | 13.80 ± 3.72 | 5.66 ± 3.25 |
|  | (0.08 ± 0.03) | (0.04 ± 0.02) |
| urine | 73.32 ± 6.46 | 86.25 ± 2.79 |

TABLE 18

Biodistribution of technetium-99m-peptide-9 in normal rats (n = 3)
* % ID/organ (% ID/g)

|  | 5 mins. | 30 mins. |
| --- | --- | --- |
| liver | 2.04 ± 0.15 | 0.75 ± 0.20 |
|  | (0.32 ± 0.02) | (0.12 ± 0.03) |
| small intestine | 2.21 ± 0.16 | 1.22 ± 0.57 |
|  | (0.33 ± 0.04) | (0.19 ± 0.09) |
| large intestine | 1.36 ± 0.06 | 0.69 ± 0.35 |
|  | (0.20 ± 0.03) | (0.10 ± 0.06) |
| stomach | 0.64 ± 0.02 | 0.23 ± 0.07 |
|  | (0.18 ± 0.01) | (0.07 ± 0.02) |
| pancreas | 0.14 ± 0.03 | 0.05 ± 0.01 |
|  | (0.44 ± 0.21) | (0.10 ± 0.03) |
| lung | 0.77 ± 0.04 | 0.25 ± 0.05 |
|  | (0.89 ± 0.04) | (0.28 ± 0.04) |
| heart | 0.32 ± 0.04 | 0.10 ± 0.01 |
|  | (0.55 ± 0.04) | (0.17 ± 0.01) |
| kidney | 9.52 ± 1.07 | 6.18 ± 0.71 |
|  | (7.76 ± 0.59) | (4.66 ± 0.90) |
| whole blood | 15.17 ± 2.20 | 4.08 ± 0.77 |
|  | (1.44 ± 0.18) | (0.39 ± 0.07) |
| the rest of the body | 57.34 ± 2.74 | 26.16 ± 3.16 |
|  | (0.47 ± 0.01) | (0.21 ± 0.03) |
| urine | 16.91 ± 4.82 | 62.02 ± 5.13 |

TABLE 19

Biodistribution of technetium-99m-peptide-9 in normal rats (n = 3)
* % ID/organ (% ID/g)

|  | 60 mins. | 180 mins. |
| --- | --- | --- |
| liver | 0.51 ± 0.06 | 0.32 ± 0.07 |
|  | (0.08 ± 0.01) | (0.05 ± 0.01) |
| small intestine | 1.00 ± 0.09 | 0.84 ± 0.05 |
|  | (0.14 ± 0.02) | (0.12 ± 0.01) |
| large intestine | 0.32 ± 0.04 | 0.33 ± 0.28 |
|  | (0.04 ± 0.00) | (0.04 ± 0.04) |
| stomach | 0.13 ± 0.02 | 0.08 ± 0.04 |
|  | (0.04 ± 0.01) | (0.02 ± 0.01) |
| pancreas | 0.03 ± 0.01 | 0.02 ± 0.01 |
|  | (0.07 ± 0.01) | (0.05 ± 0.04) |
| lung | 0.12 ± 0.01 | 0.02 ± 0.00 |
|  | (0.14 ± 0.01) | (0.02 ± 0.00) |
| heart | 0.05 ± 0.02 | 0.01 ± 0.00 |
|  | (0.08 ± 0.02) | (0.01 ± 0.00) |
| kidney | 6.08 ± 0.98 | 5.41 ± 0.41 |
|  | (4.85 ± 0.60) | (3.91 ± 0.33) |
| whole blood | 1.92 ± 0.20 | 0.37 ± 0.52 |
|  | (0.18 ± 0.00) | (0.03 ± 0.05) |
| the rest of the body | 14.28 ± 2.25 | 4.91 ± 2.47 |
|  | (0.11 ± 0.02) | (0.04 ± 0.02) |
| urine | 76.35 ± 3.30 | 87.85 ± 2.70 |

TABLE 20

Biodistribution of technetium-99m-peptide-10 in normal rats (n = 3)
* % ID/organ (% ID/g)

|  | 5 mins. | 30 mins. |
|---|---|---|
| liver | 2.15 ± 0.12 | 0.91 ± 0.11 |
|  | (0.34 ± 0.03) | (0.13 ± 0.01) |
| small intestine | 2.48 ± 0.08 | 1.22 ± 0.08 |
|  | (0.37 ± 0.06) | (0.17 ± 0.03) |
| large intestine | 1.46 ± 0.10 | 0.50 ± 0.05 |
|  | (0.24 ± 0.02) | (0.07 ± 0.01) |
| stomach | 0.64 ± 0.04 | 0.31 ± 0.09 |
|  | (0.24 ± 0.12) | (0.09 ± 0.03) |
| pancreas | 0.12 ± 0.01 | 0.06 ± 0.01 |
|  | (0.33 ± 0.02) | (0.15 ± 0.02) |
| lung | 0.85 ± 0.09 | 0.36 ± 0.07 |
|  | (0.99 ± 0.08) | (0.40 ± 0.02) |
| heart | 0.34 ± 0.08 | 0.13 ± 0.01 |
|  | (0.72 ± 0.28) | (0.22 ± 0.00) |
| kidney | 12.38 ± 2.64 | 7.37 ± 0.77 |
|  | (10.31 ± 1.94) | (5.78 ± 0.72) |
| whole blood | 14.76 ± 1.55 | 6.25 ± 1.01 |
|  | (1.41 ± 0.14) | (0.57 ± 0.10) |
| the rest of the | 60.86 ± 3.64 | 27.89 ± 0.83 |
|  | (0.49 ± 0.03) | (0.22 ± 0.01) |
| urine | 10.02 ± 5.11 | 57.65 ± 1.96 |

TABLE 21

Biodistribution of technetium-99m-peptide-10 in normal rats (n = 3)
* % ID/organ (% ID/g)

|  | 60 mins. | 180 mins. |
|---|---|---|
| liver | 0.50 ± 0.06 | 0.28 ± 0.03 |
|  | (0.08 ± 0.01) | (0.05 ± 0.01) |
| small intestine | 0.84 ± 0.12 | 0.81 ± 0.19 |
|  | (0.12 ± 0.03) | (0.13 ± 0.03) |
| large intestine | 0.42 ± 0.24 | 0.17 ± 0.07 |
|  | (0.07 ± 0.03) | (0.02 ± 0.01) |
| stomach | 0.14 ± 0.03 | 0.04 ± 0.01 |
|  | (0.05 ± 0.02) | (0.01 ± 0.00) |
| pancreas | 0.03 ± 0.00 | 0.01 ± 0.00 |
|  | (0.03 ± 0.00) | (0.03 ± 0.00) |
| lung | 0.16 ± 0.01 | 0.02 ± 0.00 |
|  | (0.18 ± 0.02) | (0.03 ± 0.00) |
| heart | 0.06 ± 0.01 | 0.01 ± 0.00 |
|  | (0.09 ± 0.02) | (0.01 ± 0.00) |
| kidney | 6.93 ± 1.60 | 6.16 ± 1.53 |
|  | (5.87 ± 1.30) | (5.10 ± 1.29) |
| whole blood | 3.16 ± 2.50 | 0.20 ± 0.23 |
|  | (0.30 ± 0.24) | (0.02 ± 0.02) |
| the rest of the body | 18.49 ± 11.54 | 3.20 ± 0.53 |
|  | (0.15 ± 0.10) | (0.03 ± 0.01) |
| urine | 70.44 ± 12.73 | 89.19 ± 1.24 |

TABLE 22

Biodistribution of technetium-99m-peptide-11 in normal rat (n = 1)
* % ID/organ (% ID/g)

|  | 5 mins. | 30 mins. |
|---|---|---|
| liver | 1.90 | 1.48 |
|  | (0.21) | (0.18) |
| small intestine | 2.24 | 1.97 |
|  | (0.23) | (0.24) |
| large intestine | 1.57 | 0.56 |
|  | (0.29) | (0.08) |
| stomach | 0.72 | 0.21 |
|  | (0.23) | (0.07) |
| pancreas | 0.13 | 0.05 |
|  | (0.24) | (0.10) |

TABLE 22-continued

Biodistribution of technetium-99m-peptide-11 in normal rat (n = 1)
* % ID/organ (% ID/g)

|  | 5 mins. | 30 mins. |
|---|---|---|
| lung | 0.86 | 0.27 |
|  | (0.73) | (0.26) |
| heart | 0.27 | 0.09 |
|  | (0.37) | (0.13) |
| kidney | 7.19 | 8.85 |
|  | (5.27) | (5.97) |
| whole blood | 19.93 | 6.74 |
|  | (1.31) | (0.46) |
| the rest of the body | 59.68 | 25.55 |
|  | (0.32) | (0.14) |
| urine | 13.62 | 56.99 |

TABLE 23

Biodistribution of technetium-99m-peptide-11 in normal rat (n = 1)
* % ID/organ (% ID/g)

|  | 60 mins. | 180 mins. |
|---|---|---|
| liver | 1.39 | 0.41 |
|  | (0.17) | (0.05) |
| small intestine | 3.88 | 4.01 |
|  | (0.46) | (0.45) |
| large intestine | 0.53 | 1.39 |
|  | (0.06) | (0.17) |
| stomach | 0.37 | 0.07 |
|  | (0.10) | (0.02) |
| pancreas | 0.06 | 0.03 |
|  | (0.08) | (0.07) |
| lung | 0.22 | 0.03 |
|  | (0.19) | (0.03) |
| heart | 0.07 | 0.01 |
|  | (0.09) | (0.02) |
| kidney | 11.10 | 13.78 |
|  | (8.45) | (10.45) |
| whole blood | 4.86 | 0.58 |
|  | (0.33) | (0.04) |
| the rest of the body | 21.31 | 19.28 |
|  | (0.12) | (0.11) |
| urine | 58.56 | 60.67 |

TABLE 24

Biodistribution of technetium-99m-peptide-12 in normal rats (n = 3)
* % ID/organ (% ID/g)

|  | 5 mins. | 30 mins. |
|---|---|---|
| liver | 2.21 ± 0.12 | 1..83 ± 0.18 |
|  | (0.31 ± 0.02) | (0.23 ± 0.02) |
| small intestine | 2.53 ± 0.07 | 2.39 ± 0.24 |
|  | (0.29 ± 0.02) | (0.24 ± 0.01) |
| large intestine | 2.34 ± 0.36 | 1.53 ± 0.57 |
|  | (0.28 ± 0.03) | (0.17 ± 0.05) |
| stomach | 1.35 ± 0.18 | 1.09 ± 0.29 |
|  | (0.42 ± 0.14) | (0.28 ± 0.08) |
| pancreas | 0.26 ± 0.02 | 0.14 ± 0.01 |
|  | (0.52 ± 0.01) | (0.28 ± 0.03) |
| lung | 1.47 ± 0.29 | 0.66 ± 0.11 |
|  | (1.52 ± 0.13) | (0.65 ± 0.08) |
| heart | 0.58 ± 0.03 | 0.26 ± 0.06 |
|  | (0.88 ± 0.01) | (0.37 ± 0.07) |
| kidney | 10.56 ± 0.22 | 10.67 ± 0.59 |
|  | (7.86 ± 0.82) | (8.42 ± 0.45) |
| whole blood | 18.37 ± 0.99 | 8.80 ± 1..86 |
|  | (1.41 ± 0.09) | (0.63 ± 0.13) |

TABLE 24-continued

Biodistribution of technetium-99m-peptide-12 in normal rats (n = 3)
* % ID/organ (% ID/g)

|  | 5 mins. | 30 mins. |
| --- | --- | --- |
| the rest of the body | 53.29 ± 4.50 (0.34 ± 0.03) | 29.24 ± 2.22 (0.18 ± 0.01) |
| urine | 15.25 ± 5.49 | 47.55 ± 4.56 |

TABLE 25

Biodistribution of technetium-99m-peptide-12 in normal rats (n = 3)
* % ID/organ (% ID/g)

|  | 60 mins. | 180 mins. |
| --- | --- | --- |
| liver | 1.93 ± 0.38 (0.27 ± 0.06) | 1.63 ± 1.03 (0.23 ± 0.16) |
| small intestine | 0.76 ± 0.04 (0.09 ± 0.02) | 4.36 ± 0.96 (0.54 ± 0.15) |
| large intestine | 0.76 ± 0.04 (0.09 ± 0.02) | 0.68 ± 0.28 (0.08 ± 0.04) |
| stomach | 0.80 ± 0.09 (0.20 ± 0.02) | 0.64 ± 0.31 (0.18 ± 0.03) |
| pancreas | 0.10 ± 0.01 (0.18 ± 0.02) | 0.05 ± 0.02 (0.11 ± 0.03) |
| lung | 0.29 ± 0.03 (0.29 ± 0.05) | 0.29 ± 0.38 (0.32 ± 0.43) |
| heart | 0.10 ± 0.04 (0.15 ± 0.05) | 0.53 ± 0.87 (0.77 ± 1.29) |
| kidney | 11.73 ± 0.38 (8.42 ± 0.09) | 11.17 ± 1.22 (7.94 ± 0.36) |
| whole blood | 3.70 ± 0.32 (0.28 ± 0.02) | 0.93 ± 0.18 (0.07 ± 0.01) |
| the rest of the body | 11.97 ± 1.79 (0.08 ± 0.01) | 5.01 ± 3.19 (0.03 ± 0.02) |
| urine | 67.51 ± 2.53 | 75.20 ± 8.16 |

TABLE 26

Biodistribution of technetium-99m-peptide-13 in normal rats (n = 3)
* % ID/organ (% ID/g)

|  | 5 mins. | 30 mins. |
| --- | --- | --- |
| liver | 1.80 ± 0.19 (0.36 ± 0.03) | 1.20 ± 0.26 (0.21 ± 0.02) |
| small intestine | 1.99 ± 0.09 (0.41 ± 0.03) | 1.62 ± 0.21 (0.29 ± 0.07) |
| large intestine | 1.25 ± 0.21 (0.27 ± 0.05) | 0.58 ± 0.27 (0.11 ± 0.04) |
| stomach | 0.56 ± 0.10 (0.37 ± 0.04) | 0.28 ± 0.04 (0.13 ± 0.02) |
| pancreas | 0.11 ± 0.02 (0.36 ± 0.05) | 0.08 ± 0.05 (0.22 ± 0.12) |
| lung | 0.81 ± 0.21 (1.05 ± 0.20) | 0.25 ± 0.04 (0.35 ± 0.03) |
| heart | 0.32 ± 0.04 (0.61 ± 0.09) | 0.11 ± 0.00 (0.21 ± 0.01) |
| kidney | 15.03 ± 0.12 (13.61 ± 0.31) | 14.35 ± 2.86 (12.15 ± 2.09) |
| whole blood | 13.68 ± 0.96 (1.68 ± 0.15) | 5.90 ± 1.52 (0.68 ± 0.17) |
| the rest of the body | 59.91 ± 6.49 (0.60 ± 0.07) | 30.85 ± 9.51 (0.30 ± 0.10) |
| urine | 10.30 ± 5.73 | 47.18 ± 10.70 |

TABLE 27

Biodistribution of technetium-99m-peptide-13 in normal rats (n = 3)
* % ID/organ (% ID/g)

|  | 60 mins. | 180 mins. |
| --- | --- | --- |
| liver | 0.70 ± 0.10 (0.13 ± 0.02) | 0.29 ± 0.05 (0.05 ± 0.01) |
| small intestine | 2.02 ± 0.20 (0.37 ± 0.05) | 4.48 ± 4.21 (0.81 ± 0.76) |
| large intestine | 0.40 ± 0.15 (0.07 ± 0.02) | 0.23 ± 0.15 (0.04 ± 0.02) |
| stomach | 0.21 ± 0.08 (0.09 ± 0.04) | 0.04 ± 0.01 (0.02 ± 0.01) |
| pancreas | 0.03 ± 0.01 (0.09 ± 0.01) | 0.02 ± 0.01 (0.05 ± 0.03) |
| lung | 0.12 ± 0.02 (0.16 ± 0.03) | 0.02 ± 0.00 (0.03 ± 0.00) |
| heart | 0.05 ± 0.01 (0.09 ± 0.02) | 0.01 ± 0.00 (0.01 ± 0.00) |
| kidney | 12.91 ± 1.56 (11.09 ± 0.84) | 10.83 ± 2.34 (8.92 ± 1.64) |
| whole blood | 2.16 ± 0.66 (0.25 ± 0.08) | 0.34 ± 0.22 (0.04 ± 0.03) |
| the rest of the body | 15.21 ± 7.91 (0.15 ± 0.08) | 2.65 ± 0.77 (0.03 ± 0.01) |
| urine | 67.15 ± 9.16 | 81.22 ± 2.17 |

TABLE 28

Biodistribution of technetium-99m-peptide-14 in normal rats (n = 3)
* % ID/organ (% ID/g)

|  | 5 mins. | 30 mins. |
| --- | --- | --- |
| liver | 2.65 ± 0.66 (0.34 ± 0.08) | 1.60 ± 0.34 (0.22 ± 0.05) |
| small intestine | 2.73 ± 0.24 (0.33 ± 0.02) | 2.34 ± 0.32 (0.32 ± 0.04) |
| large intestine | 0.72 ± 0.11 (0.19 ± 0.03) | 0.77 ± 0.10 (0.09 ± 0.01) |
| stomach | 0.29 ± 0.10 (0.40 ± 0.07) | 1.66 ± 0.19 (0.60 ± 0.04) |
| pancreas | 0.15 ± 0.01 (0.33 ± 0.03) | 0.09 ± 0.00 (0.16 ± 0.03) |
| lung | 0.81 ± 0.09 (0.81 ± 0.07) | 0.32 ± 0.05 (0.32 ± 0.03) |
| heart | 0.33 ± 0.02 (0.49 ± 0.05) | 0.11 ± 0.02 (0.17 ± 0.01) |
| kidney | 12.76 ± 2.45 (9.15 ± 2.24) | 9.09 ± 0.56 (6.76 ± 0.25) |
| whole blood | 18.10 ± 0.71 (1.40 ± 0.05) | 7.99 ± 4.33 (0.65 ± 0.34) |
| the rest of the body | 55.16 ± 1.43 (0.36 ± 0.02) | 25.86 ± 4.36 (0.18 ± 0.03) |
| urine | 12.88 ± 1.38 | 53.58 ± 3.90 |

TABLE 29

Biodistribution of technetium-99m-peptide-14 in normal rats (n = 3)
* % ID/organ (% ID/g)

|  | 60 mins. | 180 mins. |
| --- | --- | --- |
| liver | 0.97 ± 0.15 (0.14 ± 0.03) | 0.38 ± 0.02 (0.06 ± 0.01) |
| small intestine | 4.88 ± 2.18 (0.66 ± 0.25) | 5.27 ± 0.71 (0.74 ± 0.03) |
| large intestine | 0.79 ± 0.41 (0.09 ± 0.05) | 0.83 ± 0.20 (0.10 ± 0.03) |
| stomach | 0.68 ± 0.33 (0.71 ± 0.05) | 1.91 ± 0.44 (0.81 ± 0.28) |

TABLE 29-continued

Biodistribution of technetium-99m-peptide-14 in normal rats (n = 3)
* % ID/organ (% ID/g)

|  | 60 mins. | 180 mins. |
|---|---|---|
| pancreas | 0.04 ± 0.01 | 0.03 ± 0.02 |
|  | (0.08 ± 0.01) | (0.06 ± 0.05) |
| lung | 0.14 ± 0.01 | 0.04 ± 0.01 |
|  | (0.15 ± 0.01) | (0.04 ± 0.01) |
| heart | 0.05 ± 0.01 | 0.01 ± 0.00 |
|  | (0.07 ± 0.01) | (0.02 ± 0.00) |
| kidney | 8.07 ± 1.03 | 6.53 ± 1.71 |
|  | (6.07 ± 0.40) | (4.53 ± 0.92) |
| whole blood | 2.53 ± 0.61 | 0.97 ± 0.81 |
|  | (0.21 ± 0.05) | (0.08 ± 0.07) |
| the rest of the body | 14.45 ± 7.76 | 4.78 ± 0.98 |
|  | (0.10 ± 0.05) | (0.03 ± 0.01) |
| urine | 67.66 ± 8.37 | 79.71 ± 2.05 |

EXAMPLE 9

In vivo stability of technetium-99m labeled synthesized peptide

After technetium-99m-peptide-1 obtained in Example 5 has been administered to rats, they were sacrificed at the 1 hour point to collect blood. Technetium-99m-peptide-2 obtained in Example 6 was also used according to the same method as above to collect blood. The bloods obtained with respect to peptide-1 and peptide-2 were respectively centrifuged at 4000 rpm for 10 mins. to separate plasma from the bloods. The plasma was then filtered through a 0.2 µm membrane filter and was subjected to HPLC analysis. The peptides were compared with respect to in vivo stability by comparing the patterns of the HPLC with those before administration.

As a result, technetium-99m-peptide-2 showed additional plural peaks compared with the pattern of HPLC before administration, indicating that the peptide is considered to have been influenced by other materials in blood. On the other hand, technetium-99m-peptide-1, which is the peptide of the present invention, showed that a peak that had appeared at retention time of 16 minutes in the pattern of the HPLC before administration was shifted in plasma to the retention time of 12 minutes which was about 4 minute earlier than before administration, but the peak remained single in plasma but was not divided into plural peaks as was in technetium-99m-peptide-2. This suggests that technetium-99m-peptide-1 is present in a unitary state in plasma, and radiochemically more stable than technetium-99m-peptide-2. The HPLC profiles of both labeled peptides are shown in FIGS. 1 and 2.

EXAMPLE 10

Imaging of a nude mouse with laryngeal cancer using technetium-99m-labeled synthesized peptide Technetium-99m labeled peptide-14 was prepared according to the method described in Examples 1 and 6. The analytical value (number per molecule) of the amino acid composition of the obtained technetium-99m-peptide-14 is shown below together with the theoretical value (number per molecule) in parentheses.

Peptide-14=Asn: 1.1 (1), Glx: 2.0 (2), Gly: 2.1 (2), Arg: 1.9 (2), Thr: 2.0 (2), Ala: 1.9 (2), Pro: 2.1 (2), Tyr: 2.0 (2), Lys: 0.9 (1), Cys: - (1), Trp: - (1).

Then, $5 \times 10^6$ of tumor cells HEp2 (Human Epidermoid Carcinoma; ATCC No. CCL 23) were suspended in 1.0 ml of culture medium (minimum essential medium (Eagle's) with Earle's BSS, 90%; fetal bovine serum, 10%). 100 µl of the suspension was subcutaneously injected to a lateral portion of the body of BALB/C nu/nu mice (6-week old). Two weeks later, the mice were Ravonal anesthetized after confirming about 0.3 gram growth of the tumor, and 15 MBq to 20 MBq of technetium-99m-peptide-14 obtained above and technetium-99m-peptide-2 obtained in Example 7 were intravenously administered through the tails. Images were taken with a gamma camera 5 and 20 minutes later. The whole body scintigrams with respect to both peptides at the 5 minute point and the 20 minute point after administration are shown in FIGS. 3, 4, 5 and 6.

Then, the animals were immediately sacrificed to determine distribution of radioactivity in each organ using a NaI single channel counter. Ratio of Tumor [T] to muscle [M] (hereinafter referred to as "[T]/[M] ratio") was then determined. After administration, [T]/[M] ratio of technetium-99m-peptide-14 at the 20 minute point was 4.50±0.71 (n=3) whilst that of technetium-99m-peptide-2 was 3.38±0.71 (n=3). From this result, it was indicated that the binding of amino acid residue Lys to the N-terminal according to the present invention improves the image of the bodily trunk, suggesting usefulness of the peptide as a radioactive diagnostic agent.

EXAMPLE 11

In vitro stability of technetium-99m labeled synthesized peptide in human plasma Technetium-99m-peptide-8 obtained in Example 8 was mixed with 10-fold equivalent of human plasma (ROCKLAND Inc.: STERILE PLASMA containing EDTA) and the mixture was incubated at 37° C. A mixture of technetium-99m-peptide-1 obtained in Example 6 was also prepared by the same method.

The mixture was filtered through a 0.2 µm membrane filter 5 minutes and 30 minutes after the mixing, and was subjected to HPLC analysis. In vitro stability was evaluated by comparing the pattern of HPLC with that of peptide-1 before the mixing procedure. The HPLC profiles of technetium-99m-peptide-1 and of each of the above technetium-99m-labeled peptides mixed with plasma at 4° C. at the 5 and 30 minute points and at 37° C. at the 5 and 30 minute points are shown in FIGS. 7, 8, 9, 10, 11, 12, 13, 14 and 15.

TABLE 30

% of unidentified radioactive substance in plasma

|  | mins. later/4° C. | 30 mins. later/4° C. |
|---|---|---|
| Peptide-1 | 5.3 | 40.1 |
| Peptide-8 | 0 | 3.16 |

TABLE 31

% of unidentified radioactive substance in plasma

|  | mins. later/37° C. | 30 mins. later/37° C. |
|---|---|---|
| Peptide-1 | 12.4 | 59.4 |
| Peptide-8 | 0 | 2.04 |

As a result, proportion of unidentified substances confirmed by new peaks to the total radioactivity used was, in case of technetium-99m-peptide-1, 5.3% and 40% at 4° C. at the 5 and 30 minute points after the mixing procedure, respectively. On the other hand, in case of technetium-99m-peptide-8 where Arg as the 10th residue of the amino acid sequence was in D-form, the proportion was 0% and 3.2% at 4° C. at the 5 and 30 minute points after the mixing procedure, respectively.

Further, in order to evaluate influence by enzymes in plasma, the proportion of unidentified substances was obtained at 4° C. and 37° C. at the 5 minute point after the mixing procedure. In case of technetium-99m-peptide-1, the proportion was 5.3% at 4° C. at the 5-minute point after the mixing procedure and 12.5% at 37° C. at the 5-minute point after the mixing procedure. On the other hand, in case of technetium-99m-peptide-8, it was 0% at 4° C. at the 5 minute point after the mixing procedure and 0% at 37° C. at the 5 minute point after the mixing procedure, confirming that the peptide is not catabolyzed by enzymes in plasma. From the above, it was suggested that replacement of a part of the amino acid sequence with D-form amino acids could increase in vivo stability of the peptide.

EXAMPLE 12

Antigen affinity of synthesized peptide-14

The epitope VTSAPDTRPAPGST of mucin core protein, to which the conventional peptide YCAREPPTRTNAYWG is known to bind, was synthesized and further conjugated to bovine serum albumin (BSA). The conjugated peptide was used as an artificial antigen to measure antigen affinity of peptide-14 by radioimmunoassay (RIA). The assay will be described below in detail.

Each 200 μl of 10 μg/ml solution of the artificial antigen in 50 mmol sodium carbonate buffer of a pH of 9.5 was added to each of 2 ml tubes containing polystyrene beads of 6.35 mm in diameter. The tubes were stood still overnight at 4° C. Then, the inside of the tubes was washed three times by a washing agent of 0.05%(v/v) Tween 20 PBS (phosphate buffer saline, pH 7.5). In order to block the portions to which the artificial antigen is not bound of the surface of the polystyrene beads, 200 μl of 1% BSA-PBS was each added to each of the tubes. The tubes were stood still for 3 hours at room temperature. Then, the inside of the tubes was washed three times.

Peptide-14 was diluted to 500, 100, 50, 10, 5, 1, 0.5, 0.1 and 0.05 μg/ml with PBS containing 1% PRIONEX™ (an albumin substitute of Pentapharm, Ltd.). Also, an affinity antibody (mouse-type monoclonal antibody) having the sequence of peptide-3 as CDR is diluted to 15 μg/ml with the PBS containing 1% PRIONEX. Each of the diluted peptide-containing solutions was added to each of the 200 μl tubes, followed by adding thereto 100 μl of the previously-prepared antibody solution. The tubes were stood still for 3 hours. Then, the inside of the tubes was washed three times with the washing agent.

A sheep antimouse antibody labelled with iodine-125 (3.7 MBq/ml, made by Amersham Co.) was diluted 100-fold with 1% BSA-PBS. To each of the tubes, 200 μl of the diluted antimouse antibody was added. Then, the tubes were stood still for 2 hours at 37° C. Then, the inside of the tubes was washed three times with the washing agent, and radioactivity was measured by use of an auto well gammma ray counter. The results are shown in Table 30 and FIG. 16. Also, a saturation curve and a scatchard plot, both of which are derived therefrom, are shown in FIG. 17 and FIG. 18. From the above, tumor antigen affinity of peptide-14 was confirmed with an antigen affinity (Ka) being indicated to be $2.34 \times 10^7$.

FIG. 16 is a diagram showing changes of radioactivity ratio with changes in concentration of peptide when peptide-14 was used, FIG. 17 is a diagram showing a saturation curve when peptide-14 is used, and FIG. 18 is a diagram showing a scatchard plot when peptide-14 is used.

TABLE 32

Binding activity of peptide-14 (PT)

| PT (g/ml) | PT (mol/l) | −log {PT (mol/l)} | binding percentage (%) | binding amount (mol × $10^{-13}$) | binding amount/ non-binding amont |
|---|---|---|---|---|---|
| $5.0 \times 10^{-4}$ | $2.4 \times 10^{-4}$ | 3.623 | 63.669 | 11.577 | $4.9 \times 10^{-9}$ |
| $1.0 \times 10^{-4}$ | $4.8 \times 10^{-5}$ | 4.322 | 58.585 | 10.653 | $2.2 \times 10^{-8}$ |
| $5.0 \times 10^{-5}$ | $2.4 \times 10^{-5}$ | 4.623 | 60.869 | 11.068 | $4.6 \times 10^{-8}$ |
| $1.0 \times 10^{-5}$ | $4.8 \times 10^{-6}$ | 5.322 | 60.056 | 10.920 | $2.3 \times 10^{-7}$ |
| $5.0 \times 10^{-6}$ | $2.4 \times 10^{-6}$ | 5.623 | 50.293 | 9.145 | $3.8 \times 10^{-7}$ |
| $1.0 \times 10^{-6}$ | $4.8 \times 10^{-7}$ | 6.322 | 38.129 | 6.933 | $1.5 \times 10^{-6}$ |
| $5.0 \times 10^{-7}$ | $2.4 \times 10^{-7}$ | 6.623 | 42.941 | 7.808 | $3.3 \times 10^{-6}$ |
| $1.0 \times 10^{-7}$ | $4.8 \times 10^{-8}$ | 7.322 | 27.890 | 5.072 | $1.1 \times 10^{-5}$ |
| $5.0 \times 10^{-8}$ | $2.4 \times 10^{-8}$ | 7.623 | 29.517 | 5.367 | $2.3 \times 10^{-5}$ |

We claim:

1. A peptide having affinity with tumor or a salt thereof, which comprises an amino acid sequence containing 20 or less amino acid residues, said amino acid sequence being described as $X_1$-YCAREPPT-$X_2$ wherein A, C, E, P, R, T, and Y represent amino acid residues expressed by standard one-letter symbols, wherein each of amino acid residues A, C, R, and Y in the amino acid sequence YCAR may be independently in either L-form or D-form, wherein $X_2$ represents any amino acid sequence and wherein $X_1$ is a saturated or unsaturated $C_1$–$C_7$ alkyl chain substituted with 1–3 amino groups, or $X_1$ is a saturated $C_1$–$C_7$ alkyl chain which is substituted with an —OH group, a —COOH group, or a NH—C(NH)$NH_2$ group, or both an —OH and a —COOH group, and which is substituted with 1–3 amino groups.

2. A peptide having affinity with tumor or salt thereof according to claim 1, wherein $X_1$ is an amino acid residue K or R in L-form or D-form in which K and R is expressed by standard one-letter symbols.

3. A peptide having affinity with tumor or a salt thereof according to claim 1, wherein $X_1$ is an amino acid residue K in L-form or D-form, and $X_2$ is an amino acid sequence RTNAYWG in which amino acid residues R, T, N, A, Y, W and G may be independently in L-form or D-form, K, R, T, N, A, Y, W and G being expressed by standard one-letter symbols.

4. A peptide having affinity with tumor or a salt thereof according to claim 1, wherein $X_1$ is an amino acid residue K in L-form or D-form, and $X_2$ is an amino acid sequence RTNAYWGQG in which amino acid residues R, T, N, A, Y, W, G and Q may be independently in L-form or D-form, K, R, T, N, A, Y, W, G and Q being expressed by standard one-letter symbols.

5. A peptide having affinity with tumor or a salt thereof according to claim 1, the N-terminal of which is chemically modified by one selected from the group consisting of acetylation, guanidylation, amidination, reduction alkylation, carbamylation, succinylation, maleilation, acetoacetylation, nitrotroponylation, dinitrophenylation, trinitrophenylation, benzyloxycarbonylation, t-butoxycarbonylation, and 9-fluorenylmethoxycarbonylation.

6. A peptide having affinity with tumor or a salt thereof according to claim 5, the N-terminal of which is acetylated.

7. A peptide having affinity with tumor or a salt thereof according to claim 1, the C-terminal of which is chemically modified by either amidation or esterification.

8. A peptide having affinity with tumor or a salt thereof according to claim 1, the N-terminal of which is chemically modified by one selected from the group consisting of acetylation, guanidylation, amidination, reduction alkylation, carbamylation, succinylation, maleilation, acetoacetylation, nitrotroponylation, dinitrophenylation, trinitrophenylation, benzyloxycarbonylation, t-butoxycarbonylation and 9-fluorenylmethoxycarbonylation, and the C-terminal of which is chemically modified by either amidation or esterification.

9. A peptide having affinity with tumor or a salt thereof according to claim 8, the N-terminal of which is acetylated, and the C-terminal of which is amidated or esterified.

10. A radioactive metal labeled peptide, which comprises a peptide having affinity with tumor or salt thereof of any one of the preceding claims, and a radioactive metal.

11. A radioactive diagnostic agent which comprises a radioactive metal labeled peptide of claim 10.

12. A radioactive diagnostic agent according to claim 11, wherein said radioactive metal is technetium-99m.

13. A radioactive diagnostic agent according to claim 11, wherein said radioactive metal is rhenium-186 or rhenium-188.

14. A radioactive diagnostic agent according to claim 11, wherein said radioactive metal is copper-62.

15. A radioactive diagnostic agent according to claim 11, wherein said radioactive metal is indium-111.

16. A radioactive therapeutic agent, which comprises a radioactive metal labeled peptide of claim 11.

17. A radioactive therapeutic agent according to claim 16, wherein said radioactive metal is rhenium-186 or rhenium-188.

18. A radioactive therapeutic agent according to claim 16, wherein said radioactive metal is yttrium-90.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:1:

Tyr Cys Ala Arg Glu Pro Pro Thr Arg Thr Phe Ala Tyr Trp Gly Gln
1               5                   10                  15

Gly ( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: Not Relevant ( i i ) MOLECULE TYPE: peptide ( i x ) FEATURE:
        ( D ) OTHER INFORMATION: The first amino acid residue Xaa
            represents a basic organic compound
            one to three amino acid residues in
            length. The tenth amino acid
            residue Xaa represents any amino
            acid sequence.

( x i ) SEQUENCE DESCRIPTION: SEQ ID NO:2:

Xaa Tyr Cys Ala Arg Glu Pro Pro Thr Xaa
1               5                   10

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:3:

Tyr Cys Ala Arg
1

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

Arg Thr Asn Ala Tyr Trp Gly
1               5

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:5:

Arg Thr Phe Ala Tyr Trp Gly (2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

```
Arg  Thr  Asn  Ala  Tyr  Trp  Gly  Gln  Gly
 1                   5
```

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:7:

```
Arg  Thr  Phe  Ala  Tyr  Trp  Gly  Gln  Gly
 1                   5
```

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:8:

```
Lys  Tyr  Cys  Ala  Arg  Glu  Pro  Pro  Thr  Arg  Thr  Phe  Ala  Tyr  Trp  Gly
 1                   5                             10                            15
Gln  Gly
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:9:

```
Tyr  Cys  Ala  Arg  Glu  Pro  Pro  Thr  Arg  Thr  Asn  Ala  Tyr  Trp  Gly
 1                   5                             10                            15
```

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:10:

```
Tyr  Cys  Ala  Arg  Glu  Pro  Pro  Thr  Arg  Thr  Phe  Ala  Tyr  Trp  Gly
 1              5                        10                       15
```

( 2 ) INFORMATION FOR SEQ ID NO:11:

( i ) SEQUENCE CHARACTERISTICS:
        ( A ) LENGTH: 18 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:11:

```
Lys  Tyr  Cys  Ala  Arg  Glu  Pro  Pro  Thr  Arg  Thr  Asn  Ala  Tyr  Trp  Gly
 1              5                        10                       15
Gln  Gly
```

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:12:

```
Val  Thr  Ser  Ala  Pro  Asp  Thr  Arg  Pro  Ala  Pro  Gly  Ser  Thr
 1              5                        10
```